(12) United States Patent
Fujiwara et al.

(10) Patent No.: US 8,540,864 B2
(45) Date of Patent: Sep. 24, 2013

(54) METHOD OF MEASURING BLOOD COMPONENT, SENSOR USED IN THE METHOD, AND MEASURING DEVICE

(75) Inventors: Masaki Fujiwara, Ehime (JP); Teppei Shinno, Ehime (JP); Shin Ikeda, Osaka (JP)

(73) Assignee: Panasonic Corporation, Osaka (JP)

( * ) Notice: Subject to any disclaimer, the term of this patent is extended or adjusted under 35 U.S.C. 154(b) by 61 days.

(21) Appl. No.: 12/829,077

(22) Filed: Jul. 1, 2010

(65) Prior Publication Data

US 2010/0270177 A1 Oct. 28, 2010

Related U.S. Application Data

(62) Division of application No. 10/578,275, filed as application No. PCT/JP2004/018020 on Dec. 3, 2004.

(30) Foreign Application Priority Data

Dec. 4, 2003 (JP) ................................. 2003-405480

(51) Int. Cl.
*G01N 27/327* (2006.01)

(52) U.S. Cl.
USPC .................................................... 205/777.5

(58) Field of Classification Search
USPC .................. 204/403.01–403.15; 205/777.5, 205/778, 792; 600/345–348; 435/4–40.52; 422/50–99; 436/62–71, 500–548
See application file for complete search history.

(56) References Cited

U.S. PATENT DOCUMENTS 3,922,598 A 11/1975 Steuer et al. ................... 324/442
4,835,477 A 5/1989 Polaschegg et al.
(Continued)

FOREIGN PATENT DOCUMENTS

EP 0 417 796 3/1991
EP 0 537 761 4/1993
(Continued)

OTHER PUBLICATIONS

Varlan, et al., "New design technique for planar conductometric haematocrit sensors", Sensors and Actuators B 34 (1996) 258-264.

*Primary Examiner* — Luan Van
*Assistant Examiner* — Gurpreet Kaur
(74) *Attorney, Agent, or Firm* — Hamre, Schumann, Mueller & Larson, P.C.

(57) ABSTRACT

The present invention provides a method of measuring a component in blood, by which an amount of the component can be corrected accurately by measuring a hematocrit (Hct) value of the blood with high accuracy and high reliability and also provides a sensor used in the method. The sensor for measuring a component in blood has a first analysis portion and a second analysis portion. The first analysis portion has a first electrode system (11,12) and a reagent layer (14), and the reagent layer (14) has an oxidoreductase that acts on the component and a mediator. In the first analysis portion, the component in the blood is measured by causing a redox reaction of the component with the oxidoreductase in the presence of the mediator and detecting a redox current caused when a voltage is applied by the first electrode (11,12). The second analysis portion has a working electrode and a counter electrode, and a mediator is provided on the counter electrode but not on the working electrode. In the second analysis portion, a Hct value of the blood is measured by supplying the blood to the electrode system, applying a voltage to cause a current to flow, and detecting a value of the current. Using this Hct value, the amount of the component is corrected.

16 Claims, 28 Drawing Sheets

(56) References Cited

U.S. PATENT DOCUMENTS

| | | | |
|---|---|---|---|
| 4,897,162 | A | 1/1990 | Lewandowski et al. |
| 5,264,103 | A | 11/1993 | Yoshioka et al. |
| 5,385,846 | A | 1/1995 | Kuhn et al. |
| 5,463,435 | A | 10/1995 | Ezawa |
| 5,475,454 | A | 12/1995 | Ezawa |
| 5,582,697 | A | 12/1996 | Ikeda et al. |
| 6,287,451 | B1 | 9/2001 | Winarta et al. |
| 6,340,428 | B1 | 1/2002 | Ikeda et al. |
| 6,471,839 | B1 | 10/2002 | Yamamoto et al. |
| 6,541,216 | B1 | 4/2003 | Wilsey et al. |
| 6,599,407 | B2 | 7/2003 | Taniike et al. |
| 6,632,349 | B1 | 10/2003 | Hodges et al. ............... 205/792 |
| 6,875,327 | B1 | 4/2005 | Miyazaki et al. |
| 7,018,843 | B2 | 3/2006 | Heller |
| 7,338,639 | B2 | 3/2008 | Burke et al. |
| 2001/0006149 | A1 | 7/2001 | Taniike et al. |
| 2001/0050227 | A1 | 12/2001 | Yamamoto et al. |
| 2002/0048532 | A1 | 4/2002 | Lin et al. |
| 2002/0053523 | A1 | 5/2002 | Liamos et al. ............... 205/787 |
| 2002/0179442 | A1 | 12/2002 | Miyazaki et al. |
| 2003/0042150 | A1 | 3/2003 | Ryu et al. .................... 205/778 |
| 2003/0082076 | A1 | 5/2003 | Lin et al. |
| 2003/0098234 | A1 | 5/2003 | Hasegawa et al. |
| 2003/0159945 | A1 | 8/2003 | Miyazaki et al. |
| 2004/0005721 | A1 | 1/2004 | Tanike et al. ................ 436/518 |
| 2004/0040866 | A1 | 3/2004 | Miyashita et al. |
| 2004/0043477 | A1 | 3/2004 | Schibli |
| 2004/0069628 | A1 | 4/2004 | Watanabe et al. ........ 204/403.01 |
| 2004/0079652 | A1 | 4/2004 | Vreeke et al. |
| 2004/0134779 | A1 | 7/2004 | Hsu et al. ................ 204/403.03 |
| 2004/0173458 | A1 | 9/2004 | Noda et al. |
| 2004/0232009 | A1 | 11/2004 | Okuda et al. |
| 2005/0023137 | A1 | 2/2005 | Bhullar et al. |
| 2005/0023152 | A1* | 2/2005 | Surridge et al. ............. 205/775 |
| 2005/0145490 | A1 | 7/2005 | Shinno et al. |
| 2005/0164328 | A1 | 7/2005 | Kuwabata et al. |
| 2006/0224658 | A1 | 10/2006 | Sato et al. |
| 2007/0062822 | A1 | 3/2007 | Fujiwara et al. |
| 2007/0080073 | A1 | 4/2007 | Wu et al. |
| 2007/0138026 | A1 | 6/2007 | Fujiwara et al. |

FOREIGN PATENT DOCUMENTS

| | | |
|---|---|---|
| EP | 0 732 406 | 9/1996 |
| EP | 0 735 363 | 10/1996 |
| EP | 0 928 967 | 7/1999 |
| EP | 0 984 069 | 3/2000 |
| EP | 1 152 239 | 11/2001 |
| EP | 1 167 532 | 1/2002 |
| EP | 1 167 538 | 1/2002 |
| EP | 1 256 798 | 11/2002 |
| EP | 1 411 348 | 4/2004 |
| EP | 1 443 322 | 8/2004 |
| JP | 3-99254 | 4/1991 |
| JP | H11-194108 | 7/1997 |
| JP | 11-118794 | 4/1999 |
| JP | 2000-039416 | 2/2000 |
| JP | 2000-065778 | 3/2000 |
| JP | 2001-091512 | 4/2001 |
| JP | 2001-201479 | 7/2001 |
| JP | 2001-318071 | 11/2001 |
| JP | 2001-527215 | 12/2001 |
| JP | 3267933 | 1/2002 |
| JP | 3369183 | 11/2002 |
| JP | 2003-501627 | 1/2003 |
| JP | 2003-521708 | 7/2003 |
| JP | 2004-117342 | 4/2004 |
| JP | 2004-163411 | 6/2004 |
| JP | 2005-114359 | 4/2005 |
| JP | 2005-147990 | 6/2005 |
| WO | 94/29731 | 12/1994 |
| WO | 96/32883 | 10/1996 |
| WO | 97/16726 | 5/1997 |
| WO | 99/32881 | 7/1999 |
| WO | 00/73785 | 12/2000 |
| WO | 01/57510 | 8/2001 |
| WO | 02/57767 | 1/2002 |
| WO | WO02/57767 | 1/2002 |
| WO | 03/008956 | 1/2003 |
| WO | 03/034055 | 4/2003 |
| WO | 03/076919 | 9/2003 |
| WO | 03/089658 | 10/2003 |
| WO | 2004/011921 | 2/2004 |
| WO | 2005/040407 | 5/2005 |

* cited by examiner

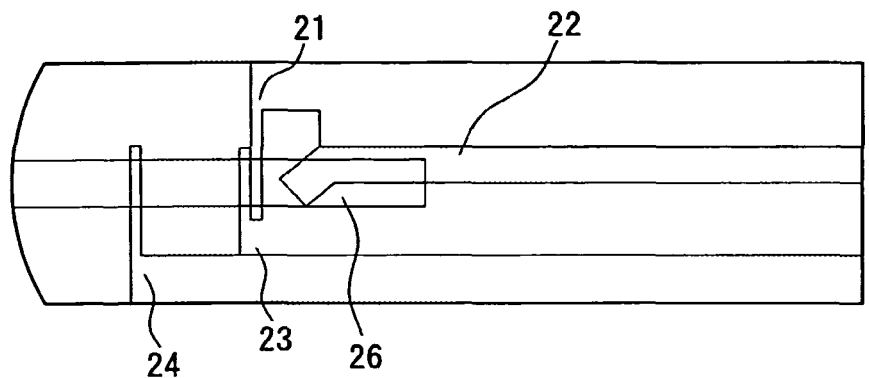
F I G. 15A
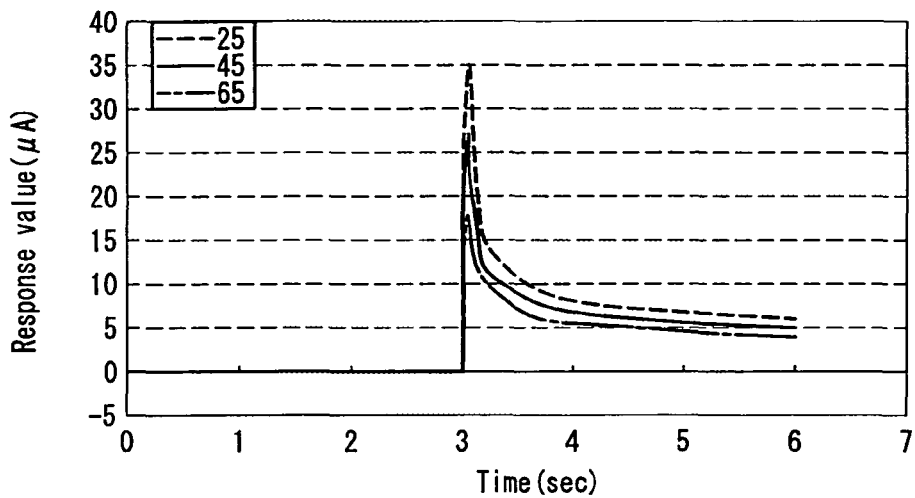
F I G. 15B
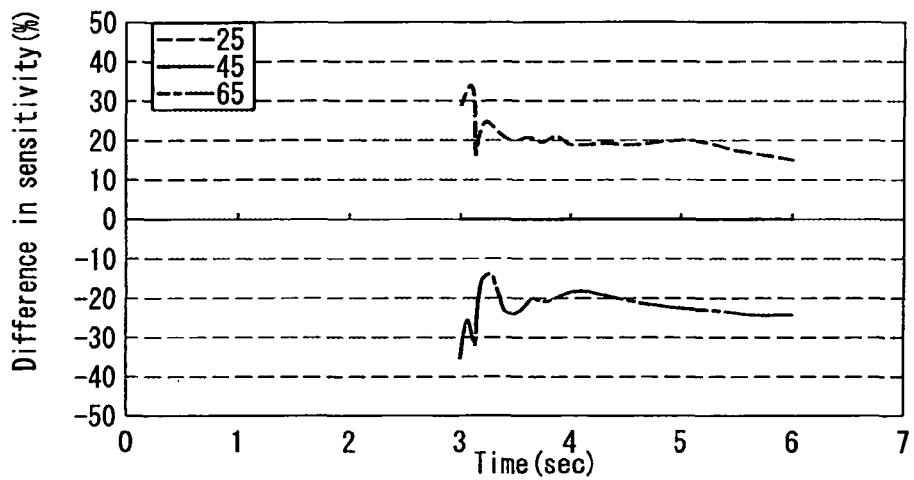
F I G. 15C

METHOD OF MEASURING BLOOD COMPONENT, SENSOR USED IN THE METHOD, AND MEASURING DEVICE

CROSS REFERENCE TO RELATED APPLICATION

This application is a Division of application Ser. No. 10/578,275, filed May 5, 2006, which is a U.S. National Stage of PCT/JP2004/018020, filed Dec. 3, 2004, which applications are incorporated herein by reference.

TECHNICAL FIELD

The present invention relates to a method of measuring a blood component, a sensor used in the method, and a measuring device.

BACKGROUND ART

Conventionally, sensors for measuring a blood component have been used for clinical tests, self-measurement of blood glucose level by diabetics, etc. The configuration of the sensor for measuring a blood component is such that, for example, a cover is disposed on an insulating substrate having a working electrode and a counter electrode on its surface with a spacer intervening between the cover and the insulating substrate. On the working electrode and the counter electrode, a reagent containing an oxidoreductase, a mediator (an electron carrier), and the like is provided, thereby forming an analysis portion. The analysis portion communicates with one end of a channel for leading blood to the analysis portion. The other end of the channel is open toward the outside of the sensor so as to serve as a blood supply port. Blood component analysis (e.g., analysis of blood glucose level) using the sensor configured as above is carried out in the following manner, for example. First, the sensor is set in a dedicated measuring device (a meter). Then, a fingertip or the like is punctured with a lancet to cause bleeding, and the blood supply port of the sensor is brought into contact with the blood that has come out. The blood is drawn into the channel of the sensor by capillary action and flows through the channel to be led to the analysis portion where the blood comes into contact with the reagent. Then, a redox reaction occurs between a component in the blood and the oxidoreductase so that a current flows via the mediator. The current is detected, and the measuring device calculates an amount of the blood component based on the detected current and displays the value obtained by the calculation.

In the above-described manner, the sensor can measure the blood component. However, since the obtained measured value might be affected by a hematocrit (Hct), it might be necessary to measure a Hct value and then correct the amount of the blood component based on this Hct value in order to obtain an accurate measured value. For example, there has been a sensor that corrects an amount of a blood component by measuring a Hct value by the use of two working electrodes and one reference electrode (see Patent Document 1). Other than this, there has been a method in which a Hct value is measured using a mediator (see Patent Document 2). However, the conventional technique has a problem concerning the accuracy and the reliability of the measured Hct value so that the amount of the blood component cannot be corrected sufficiently and accurately.
Patent Document 1: JP 2003-501627 A
Patent Document 2: Japanese Patent No. 3369183

DISCLOSURE OF INVENTION

Problem to be Solved by the Invention

With the foregoing in mind, it is an object of the present invention to provide a method of measuring a blood component, by which an amount of the blood component can be corrected sufficiently and accurately by measuring a Hct value with high accuracy and high reliability and also to provide a sensor used in the method and a measuring device.

Means for Solving Problem

In order to achieve the above object, the measurement method according to the present invention is a method of measuring a component in blood, including: causing a redox reaction between the component in the blood and an oxidoreductase in the presence of a mediator; detecting an oxidation current or a reduction current caused through the redox reaction by an electrode system; and calculating an amount of the component based on a value of the detected current. The method further includes measuring a Hct value of the blood and correcting the amount of the component using this Hct value. The measurement of the Hct value includes: providing an electrode system having a working electrode and a counter electrode; providing a mediator on the counter electrode but not on the working electrode; supplying the blood to the electrode system; applying a voltage to the electrode system in this state to cause an oxidation current or a reduction current to flow between the electrodes; detecting the oxidation current or the reduction current; and calculating the Hct value based on a value of the detected current.

Furthermore, the sensor according to the present invention is a sensor for measuring a component in blood by causing a redox reaction of the component and detecting an oxidation current or a reduction current caused through the redox reaction by an electrode. The sensor includes: a first analysis portion including a first electrode system on which at least an oxidoreductase that acts upon the component and a mediator are provided; and a second analysis portion including a second electrode system that includes a working electrode and a counter electrode, in which a mediator is provided on the counter electrode but not on the working electrode. In the first analysis portion, the component in the blood is measured by causing a redox reaction between the component and the oxidoreductase in the presence of the mediator and detecting by the first electrode system an oxidation current or a reduction current caused to flow when a voltage is applied. On the other hand, in the second analysis portion, a Hct value of the blood is measured by supplying the blood to the second electrode system, applying a voltage to the blood in this state to cause an oxidation current or a reduction current to flow between the working electrode and the counter electrode, and detecting a value of the oxidation current or the reduction current.

The measuring device according to the present invention is a measuring device for measuring a component in blood, including: means for holding the sensor of the present invention; means for applying a voltage to the first electrode system of the sensor; means for detecting an oxidation current or a reduction current flowing through the first electrode system; means for calculating an amount of the component from a value of the detected current; means for applying a voltage to the second electrode system of the sensor; means for detecting an oxidation current or a reduction current flowing through the second electrode system; and means for calculating a Hct value of the blood from a value of the detected current.

Effects of the Invention

As described above, the present invention is characterized by the measurement of a Hct value. That is, by providing a mediator only on a counter electrode in the measurement of a Hct value, the current reflecting the Hct value can be measured easily with high accuracy and high reliability. Thus, according to the measurement method, the sensor, and the measuring device of the present invention, the amount of the blood component can be corrected sufficiently and accurately because it is corrected based on the Hct value measured with high accuracy and high reliability. As a result, it is possible to obtain a highly accurate and highly reliable corrected value of the amount of the blood component.

BRIEF DESCRIPTION OF DRAWINGS

FIG. 15A shows how a reagent layer is provided in a sensor according to still another comparative example; FIG. 15B is a graph showing changes in response current (μA) obtained in Hct measurement over time during voltage application in the comparative example; and FIG. 15C is a graph showing changes in difference in sensitivity (%) over time during the voltage application in the comparative example.

Figure 1:
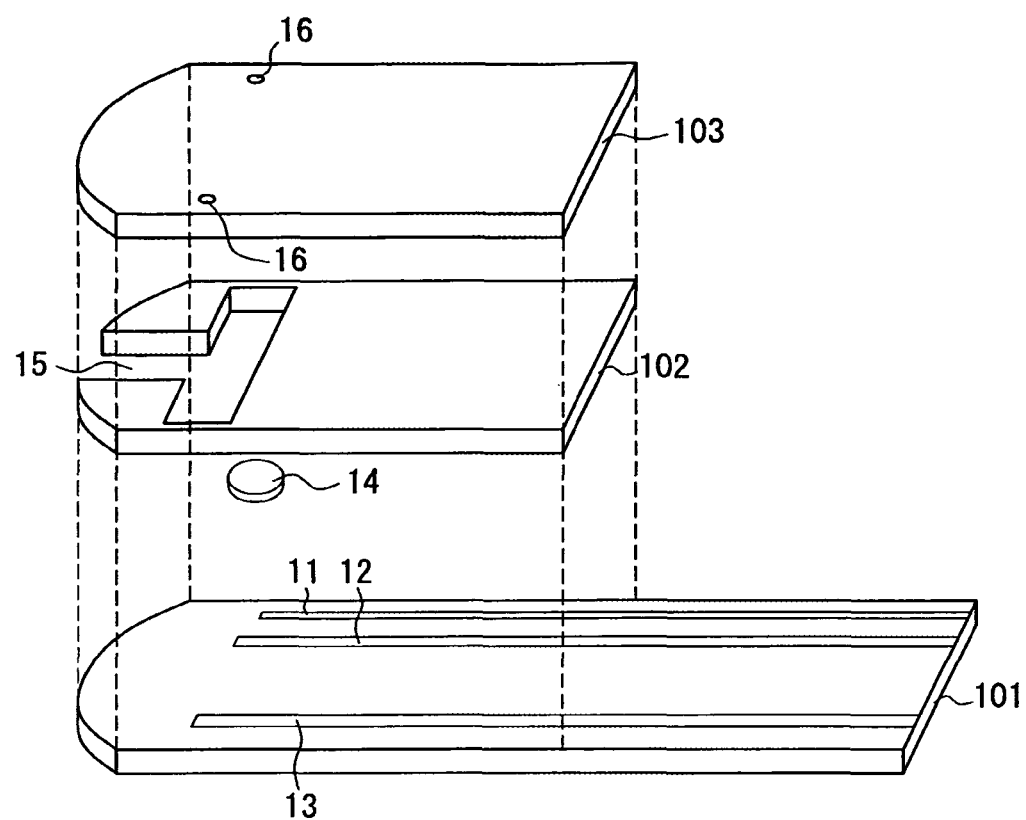
FIG. 1 is an exploded perspective view showing an example of a sensor according to the present invention.

EXPLANATION OF REFERENCE NUMERALS 11, 12, 13, 21, 22, 23, 24, 81, 82, 111, 112, 113, 114 electrode
14, 25, 83 reagent portion (reagent layer)
15, 26, 84 channel
16, 27, 85 air vent hole
101, 201, 801 insulating substrate
102, 202, 802 spacer
103, 203, 803 cover
121 sensor
122 sample supply port
130, 123 measuring device
124 display portion
125 attachment portion
131 CPU
132 LCD
133 reference voltage source
134 A/D conversion circuit
135 current/voltage conversion circuit
136 switching circuit
137a, 137b, 137c, 137d connector

DESCRIPTION OF THE INVENTION

Hereinafter, the present invention will be described in detail.

In the method of measuring a blood component and the sensor according to the present invention, the mediator used for the Hct measurement or in the second analysis portion is not particularly limited. Examples of the mediator include a ferricyanide, p-benzoquinone, p-benzoquinone derivatives, phenazine methosulfate, methylene blue, ferrocene, and ferrocene derivatives. Among these, a ferricyanide is preferable, and potassium ferricyanide is more preferable. The amount of the mediator to be blended is not particularly limited, but is, for example, 0.1 to 1000 mM, preferably 1 to 500 mM, and more preferably 10 to 200 mM per one measurement or one sensor.

In the method of measuring a blood component and the sensor according to the present invention, the electrode that is used for the Hct measurement or in the second analysis portion and on which the mediator is not provided preferably is coated with a polymeric material in order to prevent adhesion of impurities, oxidation of the electrode, and the like. Examples of the polymeric material include carboxymethyl cellulose (CMC), hydroxyethyl cellulose, hydroxypropyl cellulose, methyl cellulose, ethyl cellulose, ethyl hydroxyethyl cellulose, carboxyethyl cellulose, polyvinyl alcohol, polyvinylpyrrolidone, polyamino acid such as polylysine, polystyrene sulfonate, gelatin and derivatives thereof, polyacrylic acid and salts thereof, polymethacrylic acid and salts thereof, starch and derivatives thereof, maleic anhydride polymer and salts thereof, and agarose gel and derivatives thereof. They may be used individually or two or more of them may be used together. The method of coating the electrode with a polymeric material is not particularly limited. For example, the coating can be achieved by providing a polymeric material solution, applying the solution to the electrode surface, and then removing a solvent contained in the coating layer of the solution by drying.

In the method of measuring a blood component and the sensor according to the present invention, a voltage applied between the working electrode and the counter electrode that are used for the Hct measurement or in the second analysis portion preferably is equal to or higher than a voltage causing electrolysis of water, more preferably in the range from 1 to 10 V, and still more preferably in the range from 1 to 6.5 V. By applying a voltage that is equal to or higher than a voltage causing electrolysis of water, a current depending on a hematocrit alone can be measured with a still higher sensitivity. As a result, it is possible to obtain a stable current that is not affected by other redox substances present in blood and thus does not vary depending on a specimen (an individual). The voltage is applied for, for example, 0.001 to 60 seconds, preferably 0.01 to 10 seconds, and more preferably 0.01 to 5 seconds.

In the method of measuring a blood component and the sensor according to the present invention, it is preferable that the shortest distance between the working electrode and the counter electrode that are used for the Hct measurement or in the second analysis portion is at least 0.05 mm. When the distance between the electrodes is at least 0.05 mm as described above, the reliability of the measured value is improved. More preferably, the distance between the electrodes is at least 0.1 mm, still more preferably at least 0.5 mm.

In the method of measuring a blood component according to the present invention, the correction using the Hct value preferably is carried out based on a previously prepared calibration curve or calibration table for showing the relationship between a Hct value and an amount of the blood component.

In the method of measuring a blood component according to the present invention, the order of carrying out the blood component measurement and the Hct measurement is not particularly limited. However, in the case where the same electrode is used in both the measurements as will be described later, it is preferable that the blood component is measured first and the Hct value is measured thereafter. Note here that the case where the electrode that is used as a working electrode in the blood component measurement is used as a counter electrode in the Hct measurement corresponds to the above case. On this electrode, a mediator (e.g., potassium ferricyanide) that initially is in an oxidized state is provided. This mediator is reduced through the enzyme reaction caused in the blood component measurement and is oxidized again for the purpose of measuring the blood component. Thus, after the blood component measurement, ferricyanide ions are present dominantly at the interface of the electrode. On the other hand, it is preferable that a large amount of ferricyanide ions are present in the vicinity of a counter electrode used for the Hct measurement in order to suppress an electrolytic reduction reaction occurring at the counter electrode from being a rate-determining step. On this account, it is preferable that the electrode used as a working electrode in the blood component measurement is used as a counter electrode in the Hct measurement after the completion of the blood component measurement.

In the method of measuring a blood component according to the present invention, it is preferable that the electrode system for detecting the oxidation current or the reduction current in the measurement of the blood component includes a working electrode and a counter electrode.

Preferably, the method of measuring a blood component according to the present invention further includes measuring a temperature of a measurement environment, and the amount of the blood component is corrected using the measured temperature. This is because the enzyme reaction is affected by the temperature of the measurement environment. In this case, it is preferable that the correction using the temperature is carried out based on a previously prepared calibration curve or calibration table.

In the method of measuring a blood component and the sensor according to the present invention, the blood component to be measured is, for example, glucose, lactic acid, uric acid, bilirubin, cholesterol, or the like. Furthermore, the oxidoreductase is selected as appropriate depending on the blood component to be measured. Examples of the oxidoreductase include glucose oxidase, lactate oxidase, cholesterol oxidase, bilirubin oxidase, glucose dehydrogenase, and lactate dehydrogenase. The amount of the oxidoreductase is, for example, 0.01 to 100 U, preferably 0.05 to 10 U, and more preferably 0.1 to 5 U per one sensor or one measurement. Among these, the blood component to be measured preferably is glucose, and the oxidoreductase to be used in this case preferably is glucose oxidase or glucose dehydrogenase.

In the sensor for measuring a blood component according to the present invention, it is preferable that the first electrode system includes a working electrode and a counter electrode. Furthermore, in the sensor of the present invention, it is preferable that, in the first electrode system and the second electrode system, at least one of the electrodes or all the electrodes provided in the first electrode system also serve as the counter electrode in the second electrode system. It is more preferable that, in the first electrode system and the second electrode system, only the working electrode in the first electrode system also serves as the counter electrode in the second electrode system.

In the sensor for measuring a blood component according to the present invention, the mediator provided on the first electrode system is not particularly limited, and examples thereof include a ferricyanide, p-benzoquinone, p-benzoquinone derivatives, phenazine methosulfate, methylene blue, ferrocene, and ferrocene derivatives. Among these, a ferricyanide is preferable, and potassium ferricyanide is more preferable. The amount of the mediator to be blended is not particularly limited, but is, for example, 0.1 to 1000 mM, preferably 1 to 500 mM, and more preferably 10 to 200 mM per one measurement or one sensor.

The sensor for measuring a blood component according to the present invention preferably is configured so that it further includes an insulating substrate, the first analysis portion, the second analysis portion, and a channel for leading the blood to the analysis portions are formed on the insulating substrate, and one end of the channel is open toward the outside of the sensor so as to serve as a blood supply port. In this case, the sensor may be configured so that there is only one blood supply port and the channel branches so that ends of branched portions communicate with the analysis portions, respectively. Alternatively, the sensor may be configured so that the second analysis portion is located in the channel and the first analysis portion is located farther from the blood supply port than the second analysis portion.

Preferably, the sensor for measuring a blood component according to the present invention is configured so that it further includes a spacer and a cover and the cover is disposed on the insulating substrate via the spacer.

In the sensor for measuring a blood component according to the present invention, it is preferable that a polymeric material, an enzyme stabilizer, and a crystal homogenizing agent further are provided on the first electrode system.

The polymeric material serves to prevent adhesion of impurities to the electrode surface and oxidation of the electrode surface as well as to protect the electrode surface. Examples of the polymeric material include CMC, hydroxyethyl cellulose, hydroxypropyl cellulose, methyl cellulose, ethylcellulose, ethyl hydroxyethyl cellulose, carboxyethyl cellulose, polyvinyl alcohol, polyvinylpyrrolidone, polyamino acid such as polylysine, polystyrene sulfonate, gelatin and derivatives thereof, polyacrylic acid and salts thereof, polymethacrylic acid and salts thereof, starch and derivatives thereof, maleic anhydride polymer and salts thereof, and agarose gel and derivatives thereof. They may be used individually or two or more of them may be used together. Among these, CMC is preferable. The ratio of the polymeric material to an entire reagent solution for preparing a reagent portion is, for example, 0.001 to 10 wt %, preferably 0.005 to 5 wt %, and more preferably 0.01 to 2 wt %.

As the enzyme stabilizer, sugar alcohol can be used, for example. Examples of the sugar alcohol include chain polyhydric alcohols and cyclic sugar alcohols, such as sorbitol, maltitol, xylitol, mannitol, lactitol, reduced paratinose, arabinitol, glycerol, ribitol, galactitol, sedoheptitol, perseitol, volemitol, styracitol, polygalitol, iditol, talitol, allitol, isylitol, hydrogenated glucose syrup, and isylitol. Note here that stereoisomers, substitution products, and derivatives of these sugar alcohols also may be used as the enzyme stabilizer. These sugar alcohols may be used individually or two or more of them may be used together. Among these, maltitol is preferable. The amount of the enzyme stabilizer to be blended is, for example, in the range from 0.1 to 500 mM, preferably from 0.5 to 100 mM, and more preferably from 1 to 50 mM per one measurement or one sensor.

The crystal homogenizing agent serves to homogenize the crystal condition of the reagent portion. As the crystal homogenizing agent, an amino acid can be used, for example. Examples of the amino acid include glycine, alanine, valine, leucine, isoleucine, serine, threonine, methionine, asparagine, glutamine, arginine, lysine, histidine, phenylalanine, tryptophan, proline, sarcosine, betaine, taurine, and salts, substitution products, and derivatives of these amino acids. They may be used individually or two or more of them may be used together. Among these, glycine, serine, proline, threonine, lysine, and taurine are preferable, and taurine is more preferable. The amount of the crystal homogenizing agent to be blended is, for example, 0.1 to 1000 mM, preferably 10 to 500 mM, and more preferably 20 to 200 mM per one measurement or one sensor.

Preferably, the sensor for measuring a blood component according to the present invention is configured so that it further includes a blood detecting electrode, and the blood detecting electrode is located farther from the blood supply port than at least one of the analysis portions so that whether or not blood is supplied surely to the at least one of the analysis portions can be detected by the blood detecting electrode. It is more preferable that the blood detecting electrode is located farther from the blood supply port than both the analysis portions.

Next, the measuring device according to the present invention preferably further includes means for correcting the amount of the blood component using the Hct value. Furthermore, in the measuring device of the present invention, the voltage applied to the second electrode system preferably is equal to or higher than a voltage causing electrolysis of water, more preferably in the range from 1 to 10 V, and still more preferably from 1 to 6.5 V.

Figure 29:
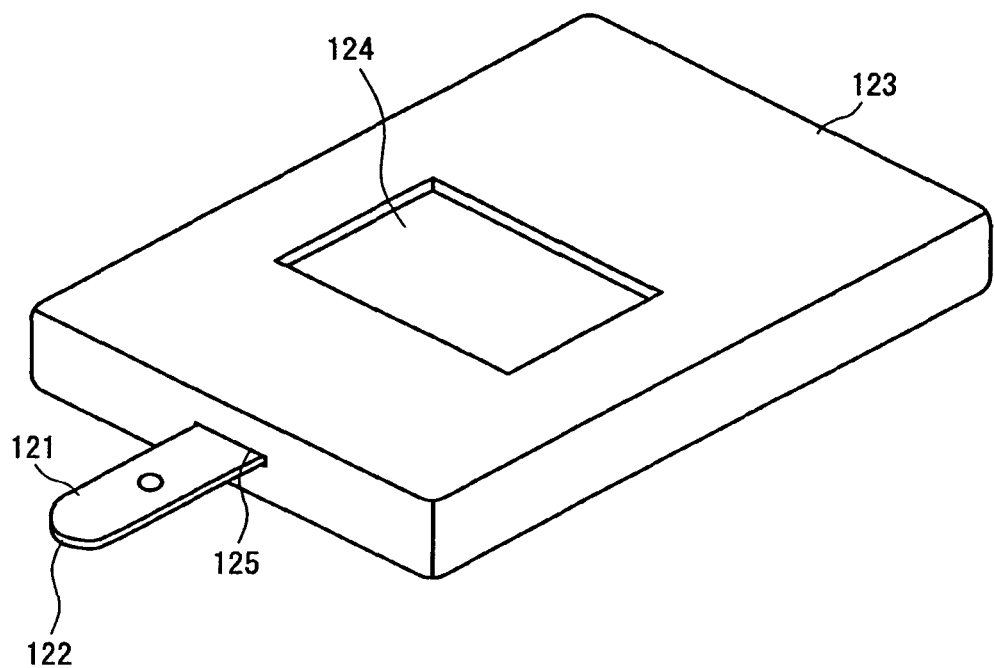
FIG. 29 is a perspective view showing an example of a measuring device according to the present invention.

FIG. 29 is a perspective view showing an example of a measuring device according to the present invention to which a sensor according to the present invention is attached. As shown in FIG. 29, this measuring device 123 has a sensor attachment portion 125 at one end, and a sensor 121 is attached to this portion so as to be held by the measuring device. The reference numeral 122 denotes a sample supply port of the sensor 121. This measuring device 123 has a display portion 124 at a substantially center portion thereof, and the result of the measurement is displayed in this display portion 124.

The measuring device according to the present invention preferably includes a connector, a switching circuit, a current/voltage conversion circuit, an A/D conversion circuit, a reference voltage source, a CPU, and a liquid crystal display portion (LCD). By providing these components, the following operations become possible: applying a voltage to the first electrode system and the second electrode system in the sensor of the present invention; detecting the value of a current flowing between these electrode systems; calculating an amount of the blood component or a Hct value based on the thus-detected current value; correcting the amount of the blood component based on the Hct value; and displaying the thus-obtained corrected value. With regard to the circuit configuration of a measuring device according to the present invention, an example thereof will be described later.

Hereinafter, examples of a sensor for measuring a blood component according to the present invention will be described with reference to the drawings.

Example 1

Figure 2:
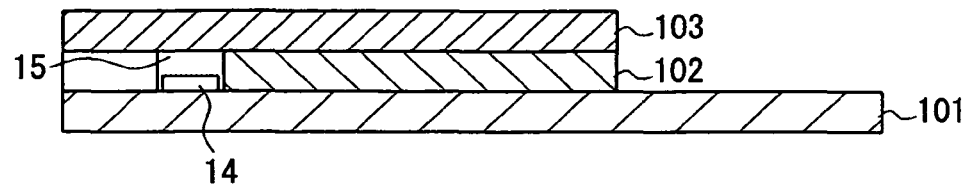
FIG. 2 is a sectional view of the sensor.
Figure 3:
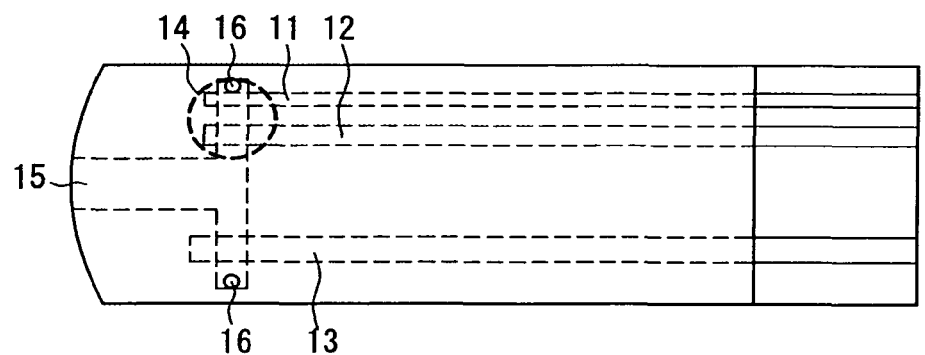
FIG. 3 is a plan view of the sensor.

FIGS. 1, 2, and 3 show one example of a sensor for measuring a blood component according to the present invention. FIG. 1 is an exploded perspective view of the sensor, FIG. 2 is a sectional view of the sensor, and FIG. 3 is a plan view of the sensor. In these three drawings, the same components are given the same reference numerals.

As shown in the drawings, in this sensor, three electrodes 11, 12, and 13 are formed on an insulating substrate 101. Each of the electrodes can be switched between a working electrode and a counter electrode. The surface of the electrode 13 is coated with a polymeric material such as CMC. On an electrode portion formed by the electrodes 11 and 12, a reagent layer 14 is disposed. The reagent layer 14 contains an oxidoreductase such as glucose dehydrogenase and a mediator, and optionally contains a polymeric material, an enzyme stabilizer, and a crystal homogenizing agent. The type and the blending ratio of these reagents are as described above. A cover 103 is disposed on the insulating substrate 101 so as to cover an entire area excluding one end portion (the end portion on the right in the drawings) with a spacer 102 intervening therebetween. This sensor has a channel 15 for leading blood to the electrode 13 and the electrodes 11 and 12. This channel 15 branches into two portions so that the channel as a whole forms a T-shape, and ends of the branched portions communicate with the electrode portions, respectively. The channel extends to the other end portion (the end portion on the left in the drawings) of the sensor and the tip thereof is open toward the outside of the sensor so as to serve as a blood supply port. The three electrodes 11, 12, and 13 are connected to leads, respectively. These leads extend to the above-described one end portion of the sensor with the tip of each lead not being covered with the cover but being exposed. The cover 103 has two air vent holes 16 at portions corresponding to the ends of the branched portions of the channel 15.

In the present invention, the material of the insulating substrate is not particularly limited, and may be, for example, polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), polymethyl methacrylate (PMMA), an ABS resin (ABS), or glass. Among these, polyethylene terephthalate (PET), polycarbonate (PC), and polyimide (PI) are preferable, and polyethylene terephthalate (PET) is more preferable. The size of the insulating substrate is not particularly limited. For example, the insulating substrate may have an overall length of 5 to 100 m, a width of 2 to 50 mm, and a thickness of 0.05 to 2 mm; preferably an overall length of 7 to 50 mm, a width of 3 to 20 mm, and a thickness of 0.1 to 1 mm; and more preferably an overall length of 10 to 30 mm, a width of 3 to 10 mm, and a thickness of 0.1 to 0.6 mm.

The electrodes and the leads on the insulating substrate may be formed by, for example, forming a conductive layer with gold, platinum, palladium, or the like by sputtering or vapor deposition and then processing the conductive layer into a particular electrode pattern with a laser. Examples of the laser include YAG lasers, $CO_2$ lasers, and excimer lasers. Note here that the electrode pattern is not limited to those shown in the examples or the like, and there is no limitation regarding the electrode pattern as long as it can achieve the effect of the present invention. The coating of the surface of the electrode 13 can be achieved by, for example, preparing a solution of the polymeric material, dropping or applying this solution with respect to the electrode surface, and then drying it. The drying may be, for example, natural drying, air drying, hot air drying, or heat drying.

The reagent portion 14 can be formed in the following manner, for example. First, 0.1 to 5.0 U/sensor of PQQ-GDH, 10 to 200 mM of potassium ferricyanide, 1 to 50 mM of maltitol, and 20 to 200 mM of taurine are dissolved in a 0.01 to 2.0 wt % CMC aqueous solution to prepare a reagent solution. The reagent solution is dropped on the electrodes 11 and 12 formed on the substrate and then is dried, thus forming the reagent portion 14. The drying may be natural drying or forced drying using warm air, for example. However, if the temperature of the warm air is too high, there is a possibility that the enzyme contained in the solution might be deactivated. Thus, the temperature of the warm air preferably is around 50° C.

In the present invention, the material of the spacer is not particularly limited. For example, the same material as that of the insulating substrate can be used. The size of the spacer also is not particularly limited. For example, the spacer may have an overall length of 5 to 100 mm, a width of 2 to 50 mm, and a thickness of 0.01 to 1 mm; preferably an overall length of 7 to 50 mm, a width of 3 to 20 mm, and a thickness 0.05 to 0.5 mm; and more preferably an overall length of 10 to 30 mm, a width of 3 to 10 mm, and a thickness of 0.05 to 0.25 mm. The spacer has a T-shaped cut-away portion that serves as the channel for leading blood. The size of the cut-away portion is as follows, for example: the length from the blood supply port to the branching part is 0.5 to 20 mm, the length from the branching part to the end of the branched portion is 1 to 25 mm, and the width is 0.1 to 5 mm; preferably the length from the blood supply port to the branching part is 1 to 10 mm, the length from the branching part to the end of the branched portion is 1.5 to 10 mm, and the width is 0.2 to 3 mm; and more preferably the length from the blood supply port to the branching part is 1 to 5 mm, the length from the branching part to the end of the branched portion is 1.5 to 5 mm, and the width is 0.5 to 2 mm. The cut-away portion may be formed, for instance, by using a laser, a drill, or the like, or by forming the spacer using a die that can form the spacer provided with the cut-away portion.

In the present invention, the material of the cover is not particularly limited. For example, the same material as that of the insulating substrate can be used. It is more preferable that a portion of the cover corresponding to the ceiling of the sample supply channel is subjected to a treatment for imparting hydrophilicity. The treatment for imparting hydrophilicity may be carried out by, for example, applying a surfactant or introducing a hydrophilic functional group such as a hydroxyl group, a carbonyl group, or a carboxyl group to the surface of the cover by plasma processing or the like. The size of the cover is not particularly limited. For example, the cover may have an overall length of 5 to 100 mm, a width of 3 to 50 mm, and a thickness of 0.01 to 0.5 mm; preferably an overall length of 10 to 50 mm, a width of 3 to 20 mm, and a thickness of 0.05 to 0.25 mm; and more preferably an overall length of 15 to 30 mm, a width of 5 to 10 mm, and a thickness of 0.05 to 0.2 mm. The cover preferably has an air vent hole. The shape of the air vent hole may be, for example, circular, oval, polygonal, or the like, and the maximum diameter thereof may be, for example, 0.01 to 10 mm, preferably 0.025 to 5 mm, and more preferably 0.025 to 2 mm. The cover may have a plurality of air vent holes. The air vent hole may be formed, for instance, by perforating the cover with a laser, a drill, or the like, or by forming the cover using a die that can form the cover provided with the air vent hole. Then, by laminating the insulating substrate, the spacer, and the cover in this order and integrating them, the sensor can be obtained. The integration can be achieved by adhering these three components with an adhesive or through heat-sealing. As the adhesive, an epoxy adhesive, an acrylic adhesive, a polyurethane adhesive, a thermosetting adhesive (a hot melt adhesive or the like), a UV curable adhesive, or the like can be used, for example.

Measurement of a blood glucose level using this sensor can be carried out in the following manner, for example. First, a fingertip or the like is punctured with a dedicated lancet to cause bleeding. On the other hand, the sensor is set in a dedicated measuring device (a meter). The blood supply port of the sensor set in the measuring device is brought into contact with the blood that has come out, so that the blood is led inside the sensor by capillary action. Then, the sensor analyzes the blood according to the following steps.

(Step 1; Detecting Specimen (Blood))

A voltage is applied between the electrode 11 and the electrode 13, and whether or not the blood is supplied to the sensor is detected by detecting the change in current accompanying the supply of the blood. After the supply of the blood has been confirmed, the subsequent step is started. Note here that the voltage applied in Step 1 is 0.05 to 1 V, for example.

(Step 2: Measuring Glucose)

After allowing glucose in the blood to react with the glucose oxidoreductase for a certain period of time, a voltage is applied between the electrode 11 as a working electrode and the electrode 12 as a counter electrode, thereby oxidizing a reduced mediator generated on the electrode 11 through the enzyme reaction. The oxidation current caused at this time is detected. The glucose is allowed to react with the oxidoreductase for, for example, 0 to 60 seconds, preferably 0.5 to 30 seconds, and more preferably 1 to 10 seconds. In Step 2, the voltage applied is, for example, 0.05 to 1 V, preferably 0.1 to 0.8 V, and more preferably 0.2 to 0.5 V, and the voltage application time is, for example, 0.01 to 30 seconds, preferably 0.1 to 10 seconds, and more preferably 1 to 5 seconds.

(Step 3: Measuring Hct Value)

By applying a voltage between the electrode 13 as a working electrode and the electrode 11 as a counter electrode, a current depending on a Hct value can be detected based on an electrolytic oxidation reaction of blood components. Note here that the detected current can be converted into a Hct value using a previously prepared calibration curve or calibration curve table. In this correction, a Hct value determined using a previously prepared calibration curve showing the relationship between a current and a Hct value may be used or alternatively, the detected current may be used as it is. In Step 3, the voltage applied is, for example, 1 to 10 V, preferably 1 to 6.5 V, and more preferably 2 to 3 V, and the voltage application time is, for example, 0.001 to 60 seconds, preferably 0.01 to 10 seconds, and more preferably 0.01 to 5 seconds. In Step 3, the oxidation current depending on a Hct value can be detected without being affected by any reagent because no mediator is provided on the electrode 13 as a working electrode, and the electrode 13 and the electrode 11 are spaced apart from each other by a certain distance with no reagent such as a mediator being provided in this space so that only blood is present in this space. Preferably, Step 3 is performed after the completion of Step 2. Although the electrode 11 is used as a counter electrode in the present example, the measurement also can be achieved when the electrode 12 is used as a counter electrode. Also, it is possible to use both the electrodes 11 and 12 as counter electrodes. Note here that when the surface of the electrode 13 is not coated with a polymeric material or the like, it is still possible to carry out the measurement.

(Step 4: Correcting Blood Component)

The amount of glucose obtained in Step 2 is corrected using the Hct value detected in Step 3. The correction preferably is carried out based on a calibration curve (including a calibration table) prepared previously. The corrected amount of glucose is displayed on or stored in the measuring device. Instead of determining the Hct value and then correcting the amount of glucose as described above, the current depending on the Hct value, which has been detected in Step 3, may be used as it is to correct the amount of glucose.

Example 2

Figure 4:
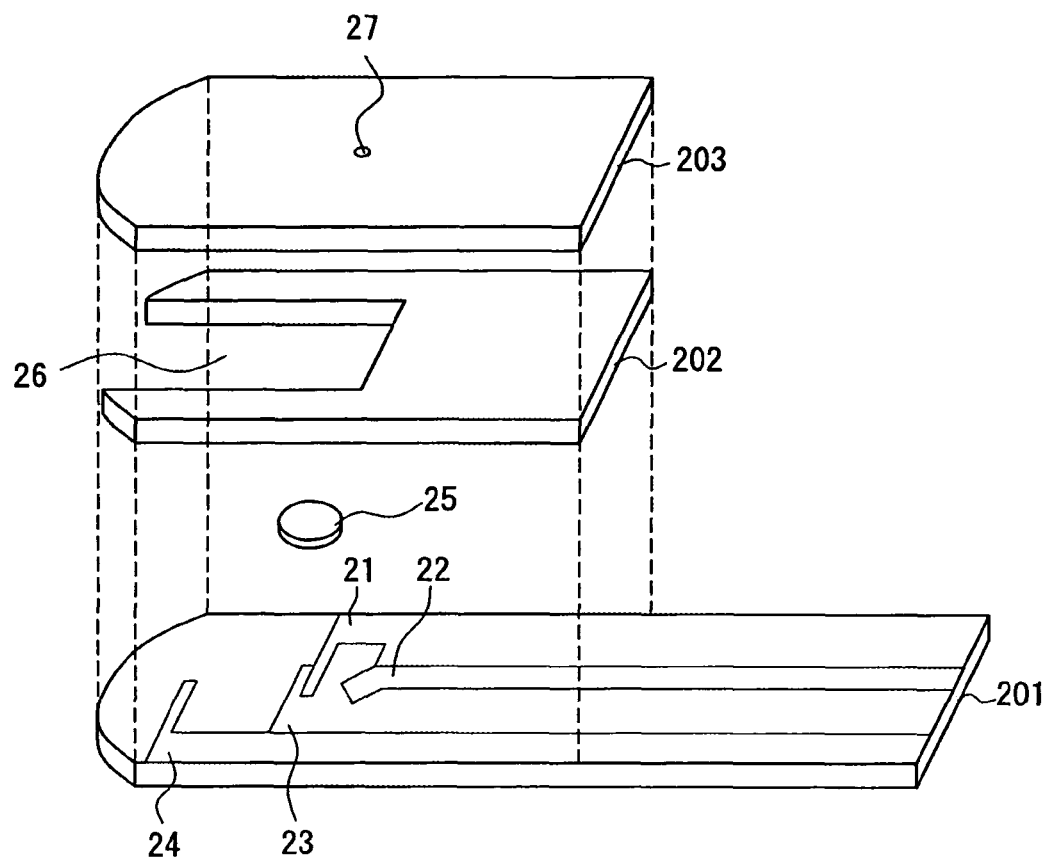
FIG. 4 is an exploded perspective view of another example of a sensor according to the present invention.
Figure 5:
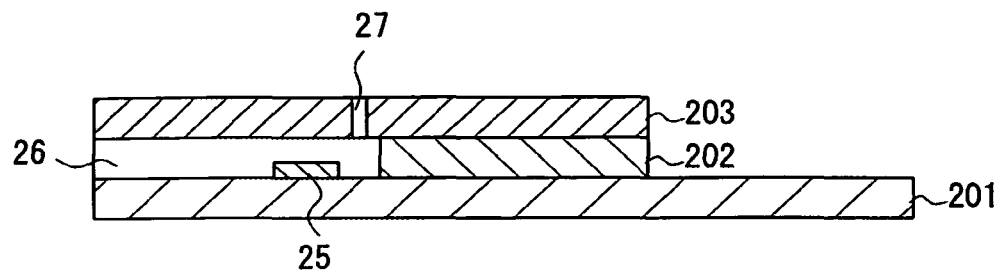
FIG. 5 is a sectional view of the sensor.
Figure 6:
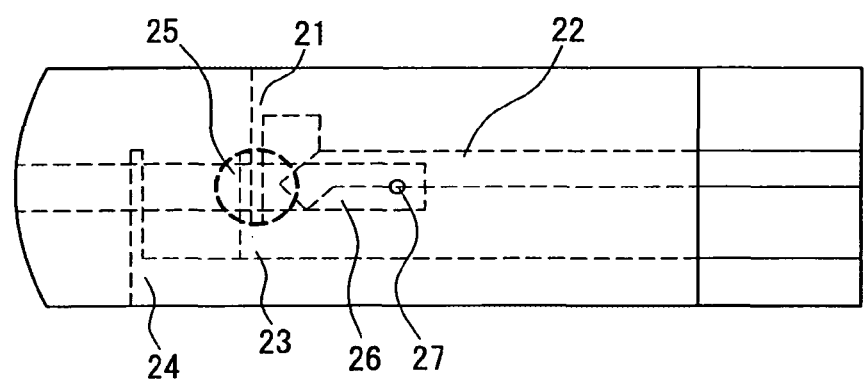
FIG. 6 is a plan view of the sensor.

FIGS. 4, 5, and 6 show another example of a sensor for measuring a blood component according to the present invention. FIG. 4 is an exploded perspective view of the sensor, FIG. 5 is a sectional view of the sensor, and FIG. 6 is a plan view of the sensor. In these three drawings, the same components are given the same reference numerals.

As shown in the drawings, in this sensor, four electrodes 21, 22, 23, and 24 are formed on an insulating substrate 201. These electrodes can be switched between a working electrode and a counter electrode. The surface of the electrode 24 is coated with a polymeric material in the manner as described above. On an electrode portion formed by the electrodes 21, 22, and 23, a reagent layer 25 is provided. The reagent layer 25 contains an oxidoreductase such as glucose dehydrogenase and a mediator, and optionally contains a polymeric material, an enzyme stabilizer, and a crystal homogenizing agent. The type and the blending ratio of these reagents are as described above. A cover 203 is disposed on the insulating substrate 201 so as to cover an entire area excluding one end portion (the end portion on the right in the drawings) with a spacer 202 intervening therebetween. This sensor has a channel 26 for leading blood to the reagent portion 25. This channel 26 extends linearly (I-shape). The channel 26 extends to the other end portion (the end portion on the left in the drawings) of the sensor and the tip thereof is open toward the outside of the sensor so as to serve as a blood supply port. The four electrodes are arranged in series in the channel, and the electrode 22 is located farthest from the blood supply port. The four electrodes 21, 22, 23, and 24 are connected to leads, respectively. These leads extend to the above-described one end portion of the sensor with the tip of each lead not being covered with the cover but being exposed. The cover 203 has an air vent hole 27 at a portion corresponding to the rear side of the channel 26.

In the present example, the material, the size, and the like of the insulating substrate are not particularly limited, and may be the same as in Example 1. Furthermore, the electrodes, the leads, the manner of coating the electrode surface with a polymeric material, and the reagent portion also are the same as in Example 1. Still further, the material and the size of the spacer and the method of processing the spacer also are the same as in Example 1. In the present example, the spacer has an I-shaped cut-away portion that serves as the channel for leading blood. The size of the cut-away portion is as follows, for example: the overall length is 0.5 to 50 mm and the width is 0.1 to 5 mm; preferably the overall length is 1 to 10 mm and the width is 0.2 to 3 mm; and more preferably the overall length is 1 to 5 mm and the width is 0.5 to 2 mm. The cut-away portion may be formed, for instance, by using a laser, a drill, or the like, or by forming the spacer using a die that can form the spacer provided with the cut-away portion. The material and the size of the cover, the treatment for imparting hydrophilicity to the cover, and the air vent hole provided in the cover are the same as in Example 1. Also, the method for producing the sensor of the present example is the same as that for producing the sensor of Example 1.

Measurement of a blood glucose level using this sensor can be carried out in the following manner, for example. First, a fingertip or the like is punctured with a dedicated lancet to cause bleeding. On the other hand, the sensor is set in a dedicated measuring device (a meter). The blood supply port of the sensor set in the measuring device is brought into contact with the blood that has come out, so that the blood is led inside the sensor by capillary action. Then, the sensor analyzes the blood according to the following steps.

(Step 1: Detecting Specimen (Blood))

Whether or not the blood is supplied to the end of the channel is detected by applying a voltage between the electrode 24 and the electrode 22. After the supply of the blood to the end of the channel has been confirmed, the subsequent step is started. In the case where the blood is not supplied to the end of the channel, the measuring device recognizes it as the lack of the amount of the specimen and displays an error message. The voltage applied in Step 1 is, for example, 0.05 to 1 V. In this case, the specimen can be detected by detecting the change in current between the electrode 22 and any one of other electrodes (21, 23, and 24).

(Step 2: Measuring Glucose)

After allowing glucose in the blood to react with the glucose oxidoreductase for a certain period of time, a voltage is applied between the electrode 21 as a working electrode and the electrode 23 as a counter electrode, thereby oxidizing a reduced mediator generated on the electrode 21 through the enzyme reaction. The oxidation current caused at this time is detected. The glucose is allowed to react with the oxidoreductase for, for example, 0 to 60 seconds, preferably 0.5 to 30 seconds, and more preferably 1 to 10 seconds. In Step 2, the voltage applied is, for example, 0.05 to 1 V, preferably 0.1 to 0.8 V, and more preferably 0.2 to 0.5 V, and the voltage application time is, for example, 0.01 to 30 seconds, preferably 0.1 to 10 seconds, and more preferably 1 to 5 seconds.

(Step 3: Measuring Hct Value)

By applying a voltage between the electrode 24 as a working electrode and the electrode 21 as a counter electrode, a current depending on a Hct value can be detected. Based on the detected current, the Hct value of the blood can be determined. The thus determined Hct value is used for the correction in the measurement of glucose. In this correction, a Hct value determined using a previously prepared calibration curve showing the relationship between a current and a Hct value may be used or alternatively, the detected current may be used as it is. In Step 3, the voltage applied is, for example, 1 to 10 V, preferably 1 to 6.5 V, and more preferably 2 to 3 V, and the voltage application time is, for example, 0.001 to 60 seconds, preferably 0.01 to 10 seconds, and more preferably 0.01 to 5 seconds. In Step 3, the oxidation current depending on a Hct value can be detected without being affected by any reagent because no mediator is provided on the electrode 24 as a working electrode, and the electrode 24 and the electrode 21 are spaced apart from each other by a certain distance with no reagent such as a mediator being provided in this space so that only blood is present in this space. Preferably, Step 3 is performed after the completion of Step 2. Although the electrode 21 alone is used as the counter electrode in the present example, the present invention is not limited thereto. It should be noted that the electrode 23 alone, the electrode 22 alone, the combination of the electrode 21 and the electrode 22, the combination of the electrode 21 and the electrode 23, the combination of the electrode 22 and the electrode 23, the combination of the electrode 21, the electrode 22, and the electrode 23 also may be used as the counter electrode. Also, it should be noted that when the surface of the electrode 13 is not coated with a polymeric material or the like, it is still possible to achieve the measurement.

(Step 4: Correcting Blood Component)

The amount of glucose obtained in Step 2 is corrected using the Hct value detected in Step 3. The correction preferably is carried out based on a calibration curve (including a calibration table) prepared previously. The corrected amount of glucose is displayed on or stored in the measuring device.

Example 3

In the present example, six types of sensors (3-1 to 3-6) were produced so that they were different from each other in the arrangement of a reagent layer containing a mediator with respect to a working electrode or a counter electrode used for Hct measurement, and the response current and the difference in sensitivity were measured using these sensors. Also, as sensors according to Comparative Example 1, three types of sensors (3-7 to 3-9) were produced so that they were different from each other in the arrangement of a reagent layer containing a mediator with respect to a working electrode or a counter electrode used for Hct measurement, and the response current and the difference in sensitivity were measured using these sensors. The preparation of the specimens (blood), the measurement of glucose, and the correction of the blood component were carried out in the same manner as in Example 2. The above-described respective sensors were produced basically in the same manner as in Example 2 except for the arrangement of the reagent layer. The reagent layer was produced by dissolving potassium ferricyanide (amount: 60 mM) and taurine (80 mM) in a CMC aqueous solution (0.1 wt %) to prepare a reagent solution, dropping the reagent solution on the electrodes, and then drying it. The distance between the working, electrode and the counter electrode was set to be at least 0.1 mm. Furthermore, three types of blood samples whose Hct values were adjusted to be 25, 45, and 65, respectively, were provided. With regard to each of these three blood samples, a current flowing between the electrodes of the sensor when a voltage of 2.5 V was applied for 3 seconds was measured using the sensor, and the response current value and the difference in sensitivity in the Hct value measurement were determined. FIGS. 7 to 15 show the arrangement patterns of the reagent layers in the respective sensors and the measurement results. In FIGS. 7 to 15, FIGS. 7A to 15A show the arrangement pattern of the reagent layer 25, FIGS. 7B to 15B are graphs each showing changes in response current (μA) over time during the application of the voltage (V), and FIGS. 7C to 15C are graphs each showing changes in difference in sensitivity (%) over time during the application of the voltage (V). In FIGS. 7 to 15, the same components as those shown in FIGS. 4 to 6 are given the same reference numerals.

(3-1)

Figure 7A:
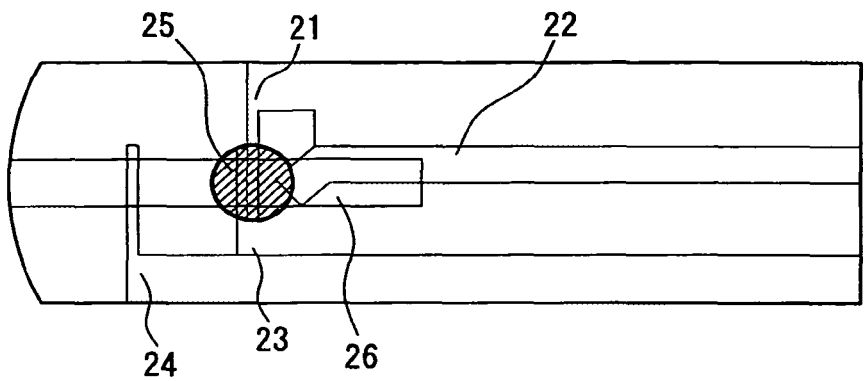
FIG. 7A shows how a reagent layer is provided in still another example of a sensor according to the present invention.
Figure 7B:
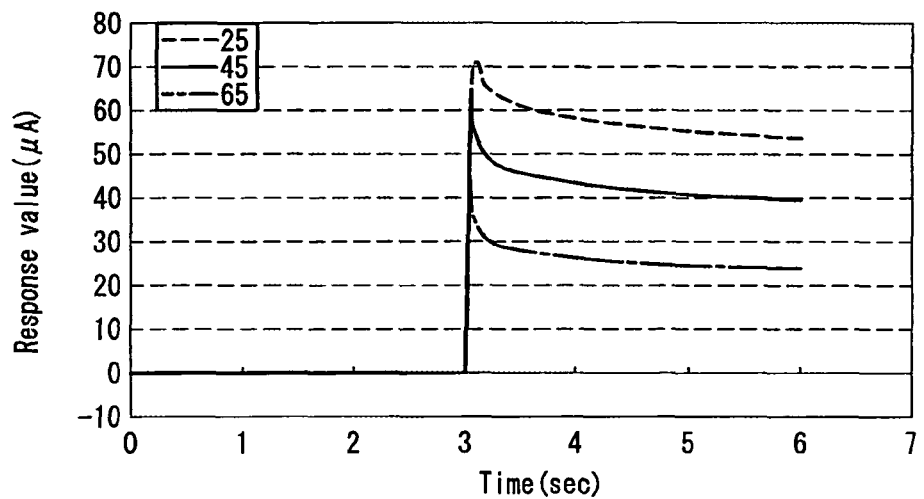
FIG. 7B is a graph showing changes in response current (μA) obtained in Hct measurement over time during voltage application in the example.
Figure 7C:
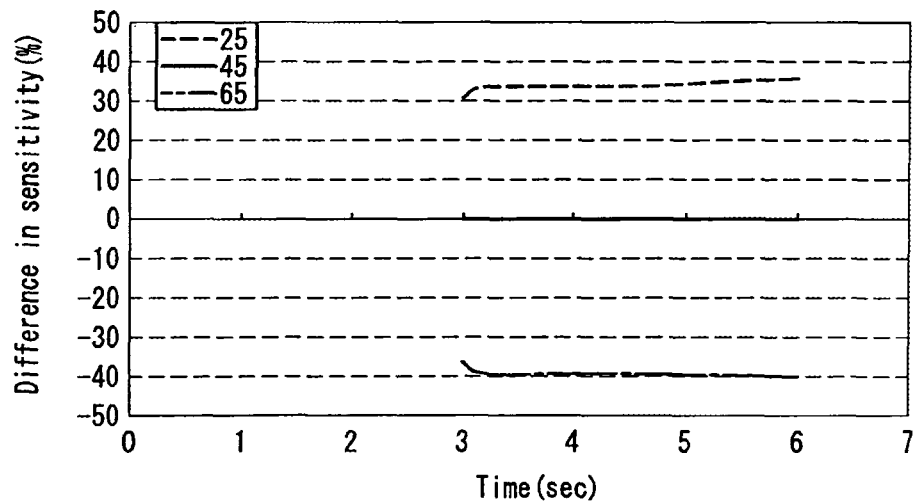
FIG. 7C is a graph showing changes in difference in sensitivity (%) over time during the voltage application in the example.

As shown in FIG. 7A, in the sensor of this example, the reagent layer 25 was provided so as to extend to the outside of the counter electrode 21 used for the Hct measurement, so that the reagent layer 25 was present on the surface of the counter electrode 21 and at a portion on the counter electrode side between the electrodes used for the blood component measurement. The graphs of FIGS. 7B and 7C show the results of the measurement of the current flowing between the electrodes of this sensor. As shown in FIGS. 7B and 7C, according to this sensor, the difference in sensitivity did not depend on the voltage application time, so that the response current reflecting the Hct value could be detected definitely and favorably.

(3-2)

Figure 8A:
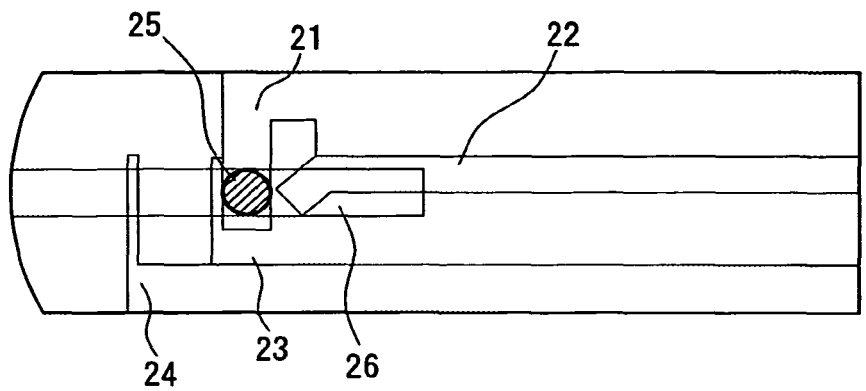
FIG. 8A shows how a reagent layer is provided in still another example of a sensor according to the present invention.
Figure 8B:
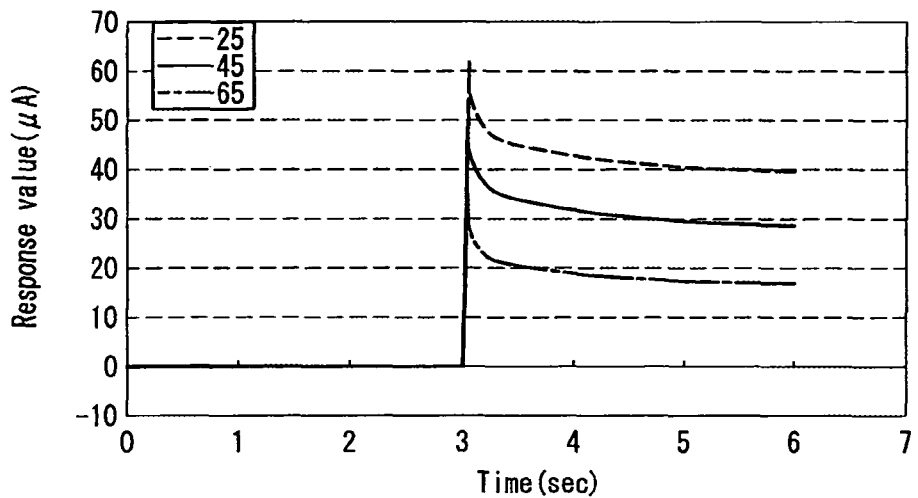
FIG. 8B is a graph showing changes in response current (μA) obtained in Hct measurement over time during voltage application in the example.
Figure 8C:
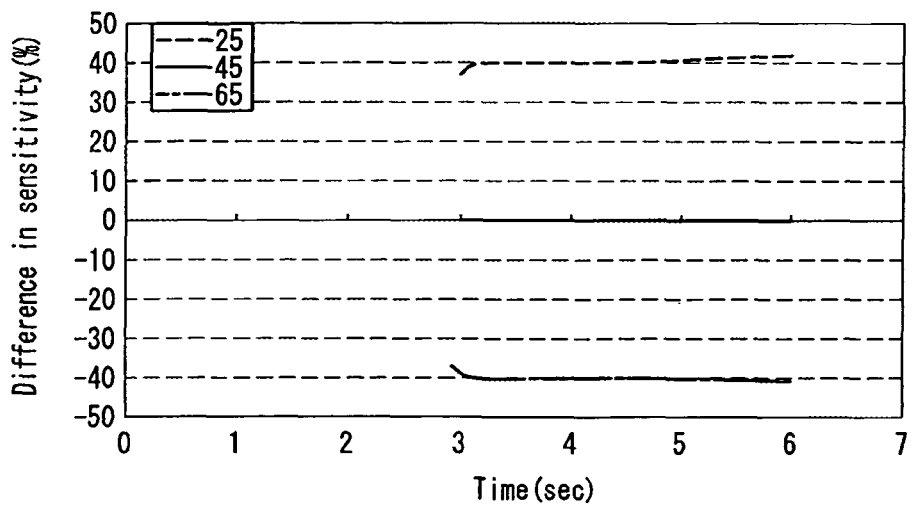
FIG. 8C is a graph showing changes in difference in sensitivity (%) over time during the voltage application in the example.

As shown in FIG. 8A, in the sensor of this example, the reagent layer 25 was provided only on the surface of the counter electrode 21. The graphs of FIGS. 8B and 8C show the results of the measurement of the current flowing between the working electrode 24 and the counter electrode 21 of this sensor. As shown in FIGS. 8B and 8C, according to this sensor, the difference in sensitivity did not depend on the voltage application time, so that the response current reflecting the Hct value could be detected definitely and favorably.

(3-3)

Figure 9A:
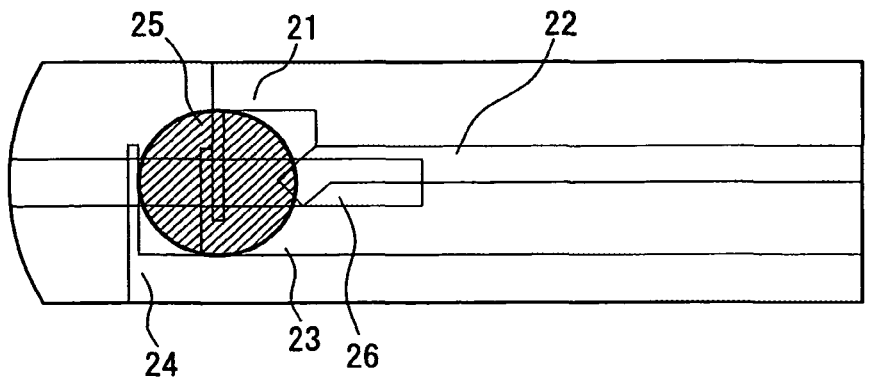
FIG. 9A shows how a reagent layer is provided in still another example of a sensor according to the present invention.
Figure 9B:
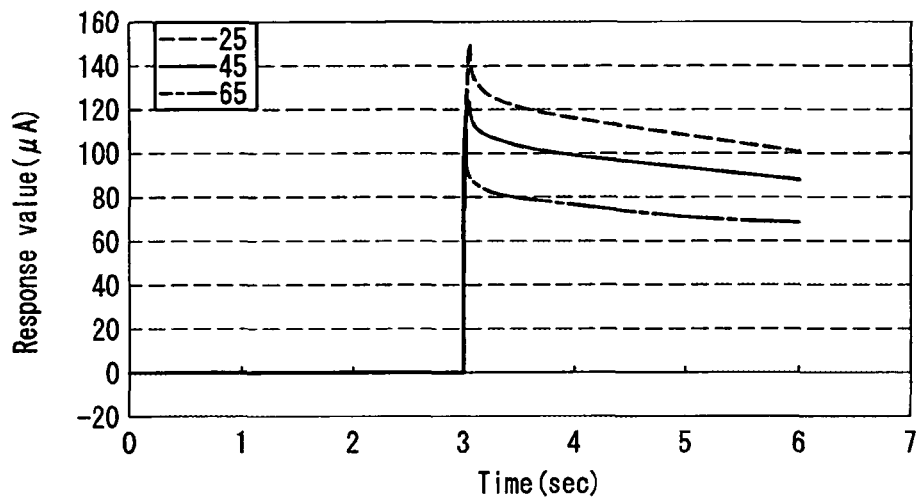
FIG. 9B is a graph showing changes in response current (μA) obtained in Hct measurement over time during voltage application in the example.
Figure 9C:
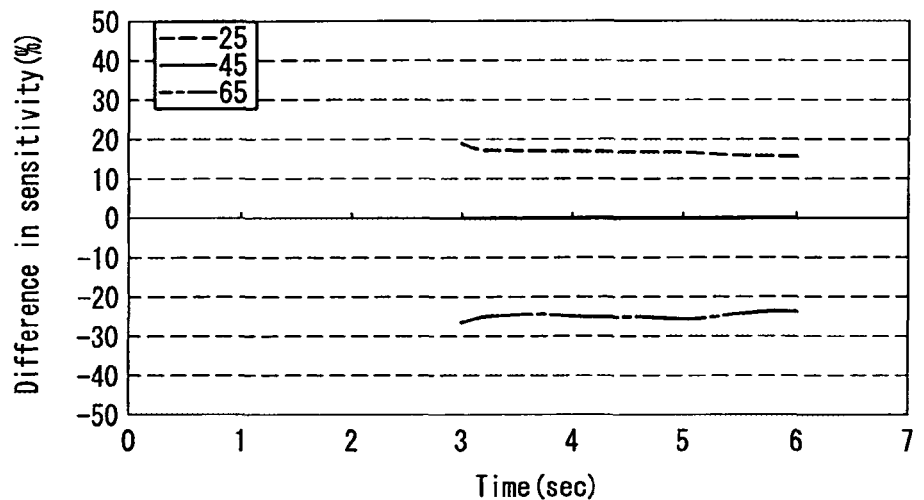
FIG. 9C is a graph showing changes in difference in sensitivity (%) over time during the voltage application in the example.

As shown in FIG. 9A, in the sensor of this example, the reagent layer 25 was provided so as to extend to the outside of the counter electrode 21, so that the reagent layer 25 was present on the surface of the counter electrode 21 and between the electrodes. Note here that no redox substance was present on the working electrode 24. The graphs of FIGS. 9B and 9C show the results of the measurement of the current flowing between the electrodes of this sensor. As shown in FIGS. 9B and 9C, according to this sensor, the difference in sensitivity did not depend on the voltage application time, so that the response current reflecting the Hct value could be detected definitely.

(3-4)

Figure 10A:
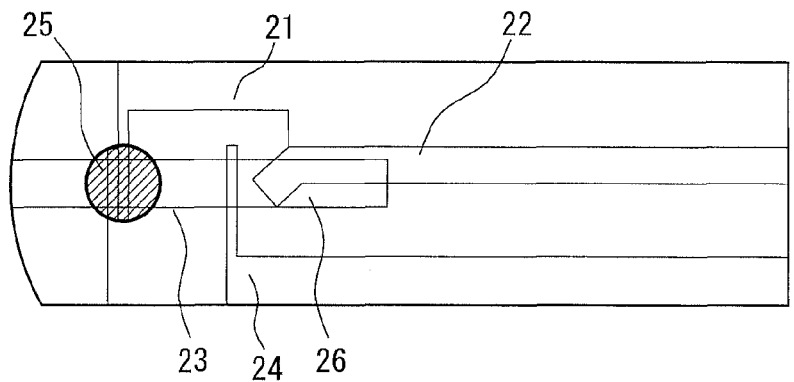
FIG. 10A shows how a reagent layer is provided in still another example of a sensor according to the present invention.
Figure 10B:
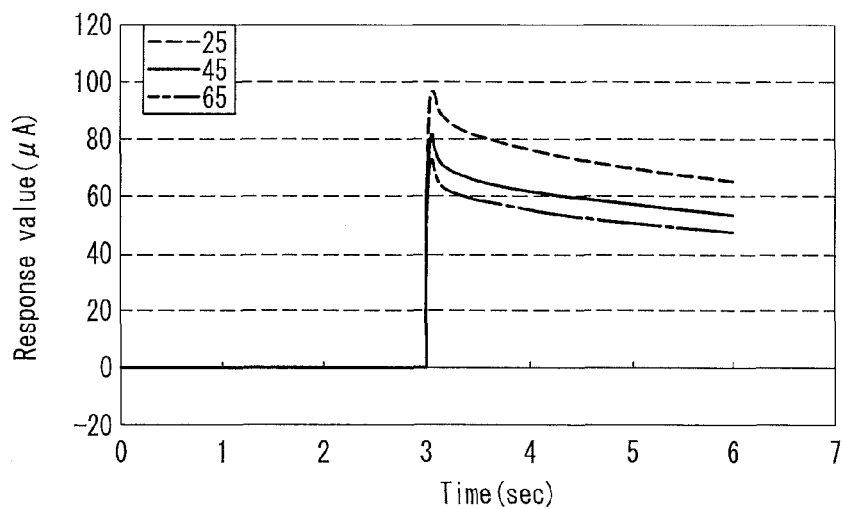
FIG. 10B is a graph showing changes in response current (μA) obtained in Hct measurement over time during voltage application in the example.
Figure 10C:
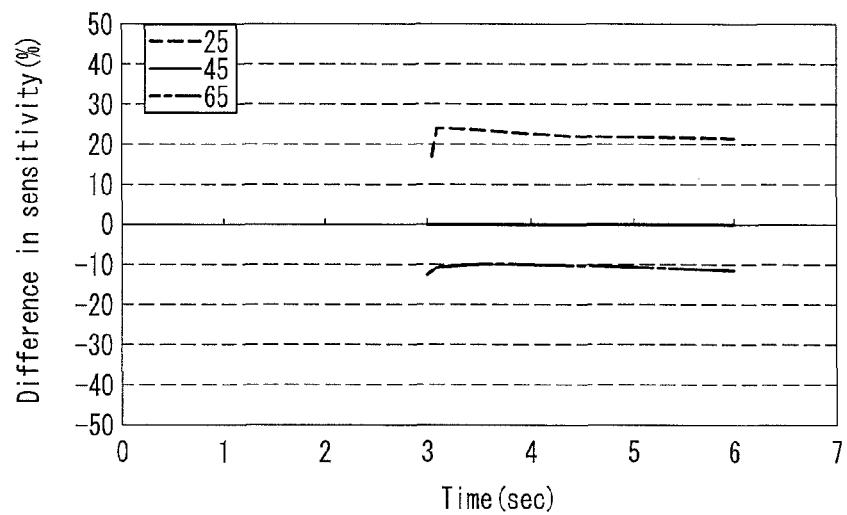
FIG. 10C is a graph showing changes in difference in sensitivity (%) over time during the voltage application in the example.

As shown in FIG. 10A, in the sensor of this example, the positions of the working electrode 24 and the counter electrode 21 that were used for the Hct measurement were switched so that the reagent layer 25 was formed on the surface of the counter electrode 21 and at a portion on the counter electrode side between the electrodes used for the blood component measurement. The graphs of FIGS. 10B and 10C show the results of the measurement of the current flowing between the electrodes of this sensor. As shown in FIGS. 10B and 100, according to this sensor, the difference in sensitivity did not depend on the voltage application time, so that the response current reflecting the Hct value could be detected definitely. However, the difference in sensitivity was slightly smaller than those exhibited by the sensors according to the examples (3-1), (3-2), and (3-3).

(3-5)

Figure 11A:
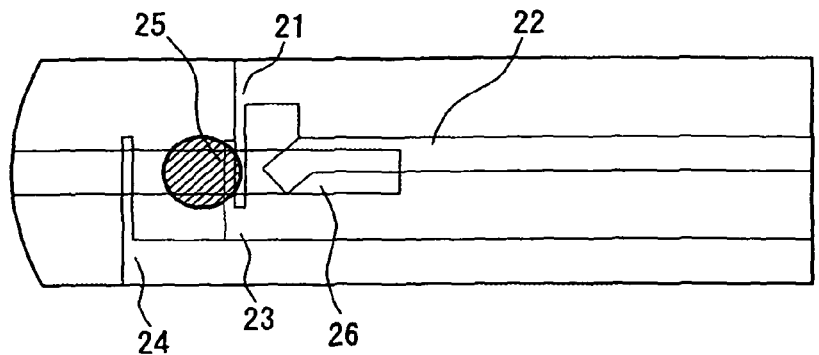
FIG. 11A shows how a reagent layer is provided in still another example of a sensor according to the present invention.
Figure 11B:
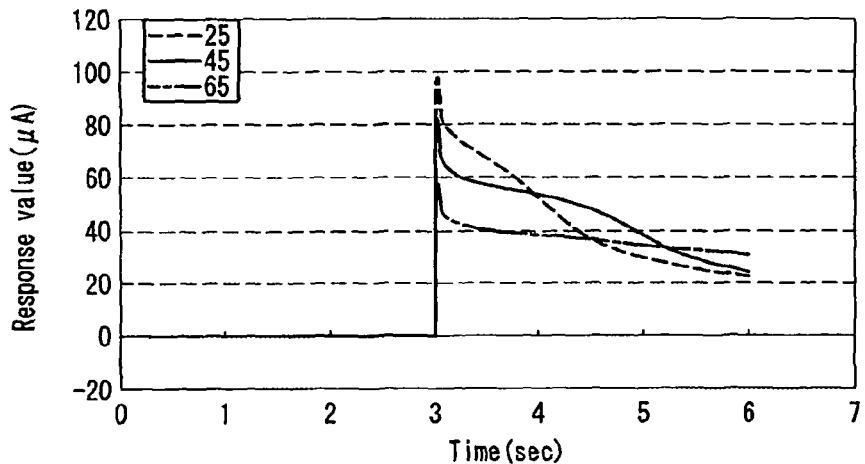
FIG. 11B is a graph showing changes in response current (μA) obtained in Hct measurement over time during voltage application in the example.
Figure 11C:
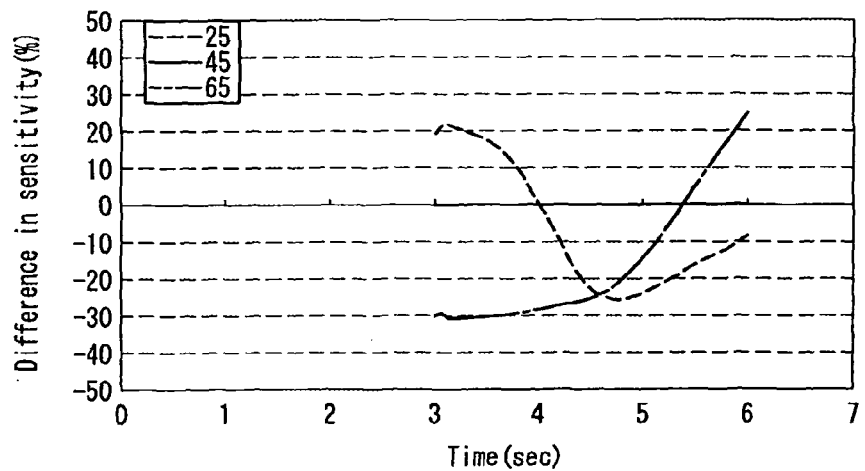
FIG. 11C is a graph showing changes in difference in sensitivity (%) over time during the voltage application in the example.

As shown in FIG. 11A, in the sensor of this example, the reagent layer 25 was provided so as to extend to the outside of the counter electrode 21, so that the reagent layer 25 was present on a part of the surface of the counter electrode 21 and at a portion between the electrodes. The graphs of FIGS. 11B and 11C show the results of the measurement of the current flowing between the electrodes of this sensor. As shown in FIGS. 11B and 11C, according to this sensor, for one second immediately after the start of the voltage application (i.e., one second between third to fourth seconds in the drawings), the response current reflecting the Hct value could be detected definitely.

(3-6)

Figure 12A:
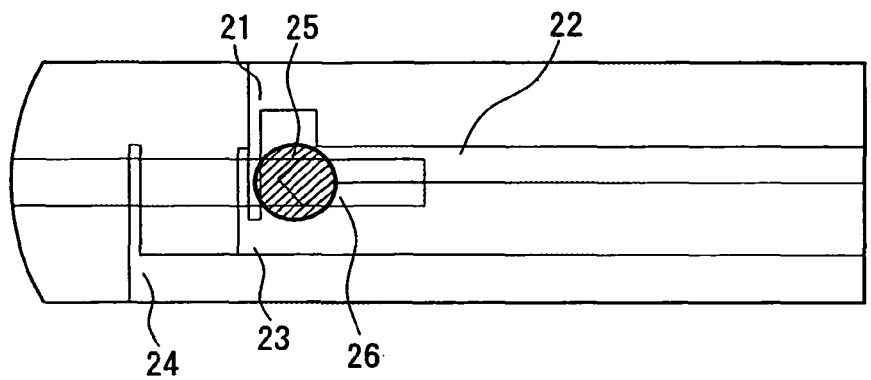
FIG. 12A shows how a reagent layer is provided in still another example of a sensor according to the present invention.
Figure 12B:
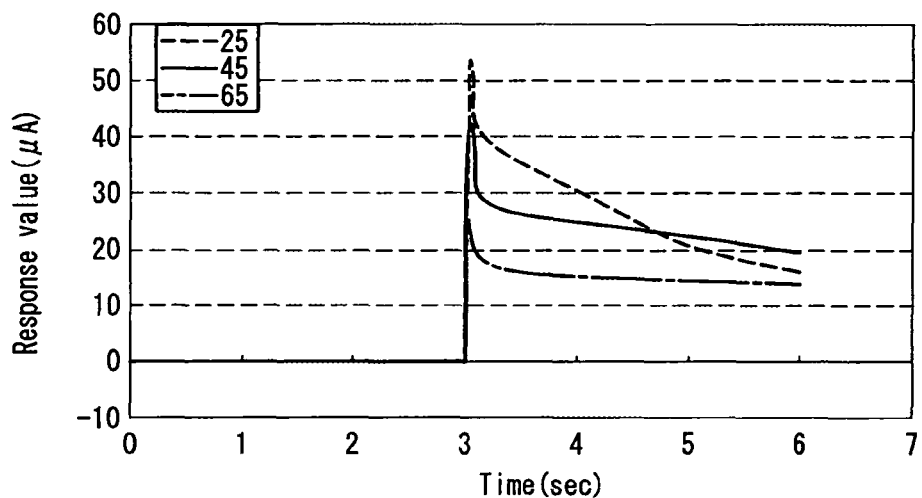
FIG. 12B is a graph showing changes in response current (μA) obtained in Hct measurement over time during voltage application in the example.
Figure 12C:
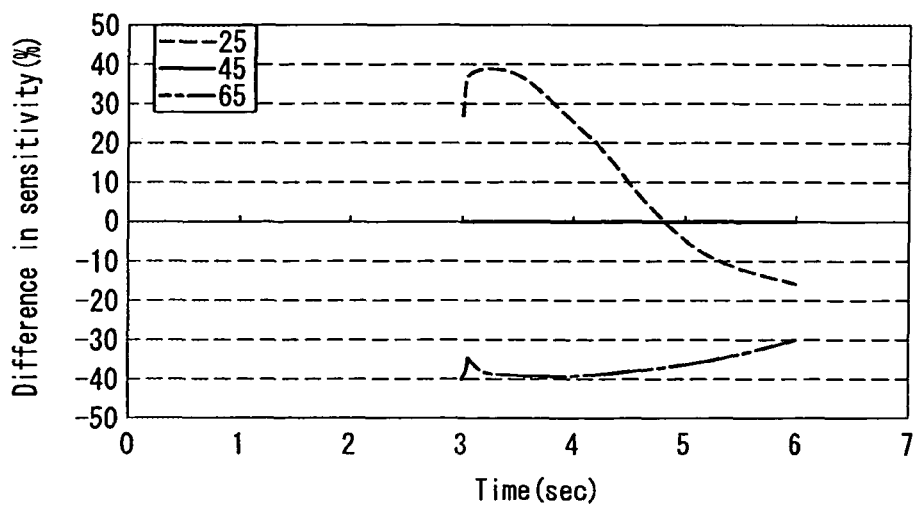
FIG. 12C is a graph showing changes in difference in sensitivity (%) over time during the voltage application in the example.

As shown in FIG. 12A, in the sensor of this example, the reagent layer 25 was provided so as to extend to the outside of the counter electrode 21, so that the reagent layer 25 was present on a part of the surface of the counter electrode 21. Note here that no redox substance was present between the electrodes. The graphs of FIGS. 12B and 12C show the results of the measurement of the current flowing between the electrodes of this sensor. As shown in FIGS. 12B and 12C, according to this sensor, for one second immediately after the start of the voltage application (i.e., one second between third to fourth seconds in the drawings), the response current reflecting the Hct value could be detected definitely.

(3-7)

Figure 13A:
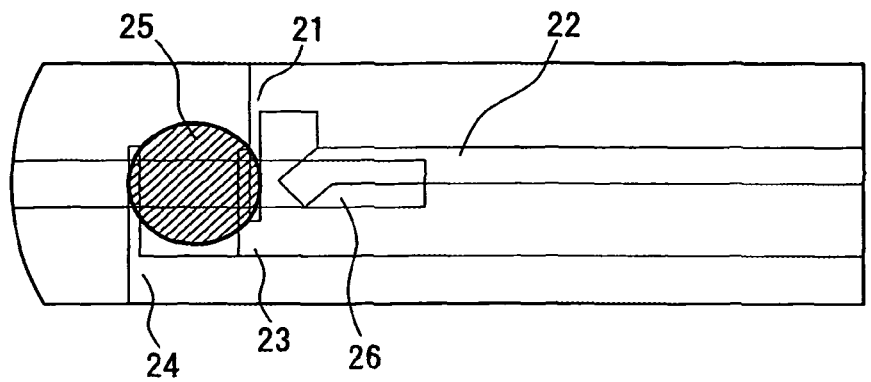
FIG. 13A shows how a reagent layer is provided in a sensor according to a comparative example.
Figure 13B:
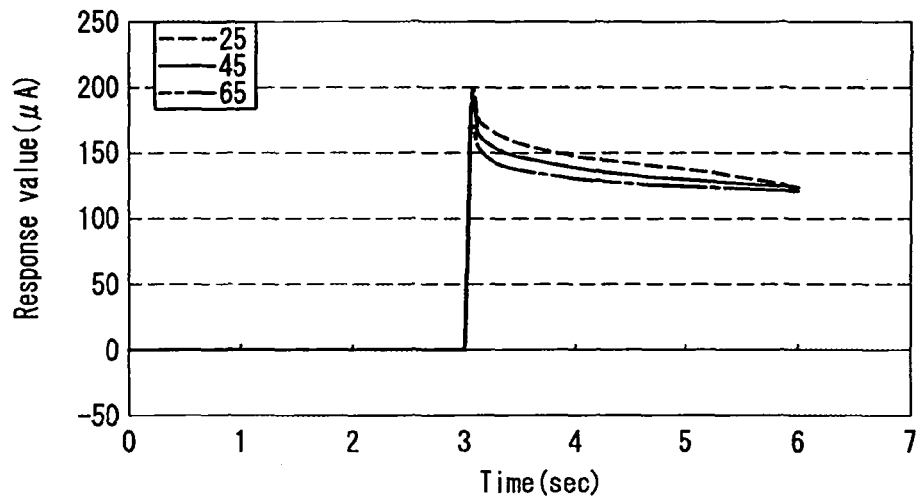
FIG. 13B is a graph showing changes in response current (μA) obtained in Hct measurement over time during voltage application in the comparative example.
Figure 13C:
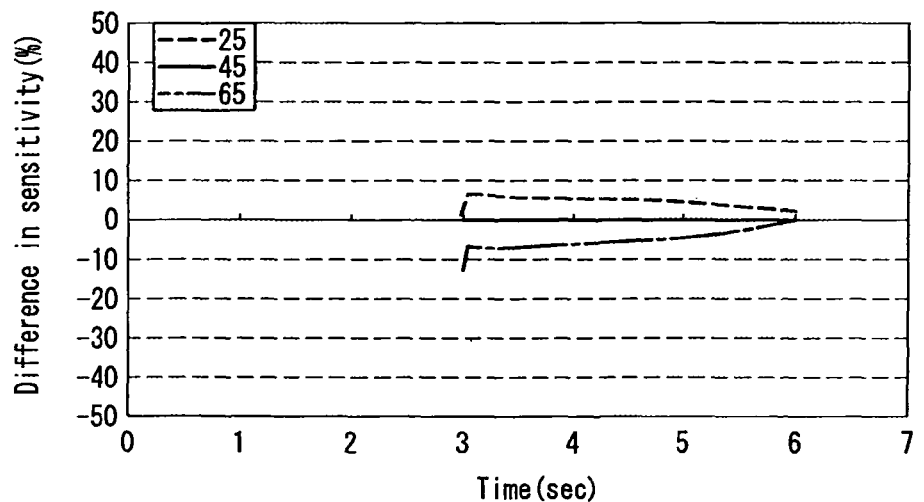
FIG. 13C is a graph showing changes in difference in sensitivity (%) over time during the voltage application in the comparative example.

As shown in FIG. 13A, in the sensor of this comparative example, the reagent layer 25 was provided so as to lie over the working electrode 24, the counter electrode 21, and the entire region between these electrodes. The graphs of FIGS. 13B and 13C show the results of the measurement of the current flowing between the electrodes of this sensor. As shown in FIGS. 13B and 13C, according to this sensor, the response current reflecting the Hct value could not be detected definitely.

(3-8)

Figure 14A:
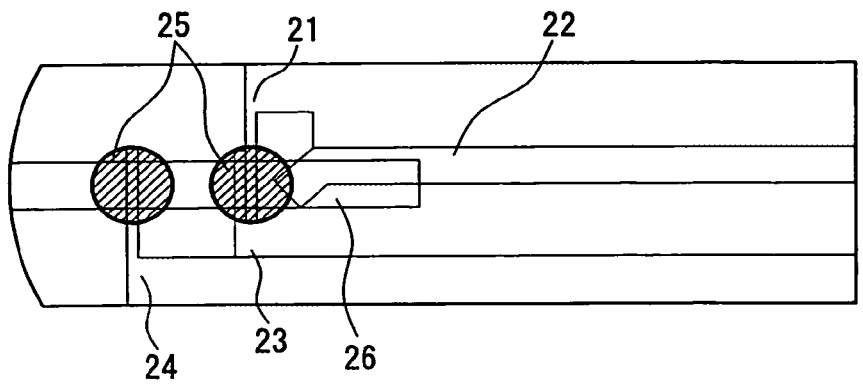
FIG. 14A shows how a reagent layer is provided in a sensor according to another comparative example.
Figure 14B:
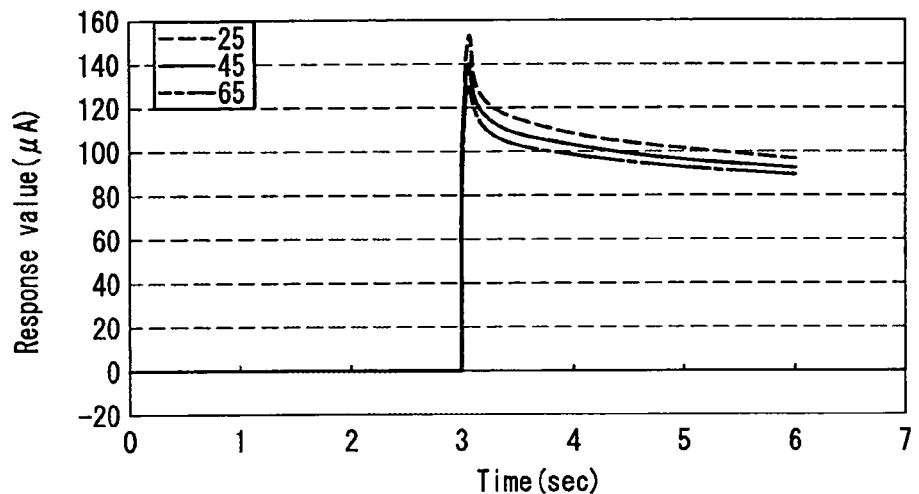
FIG. 14B is a graph showing changes in response current (μA) obtained in Hct measurement over time during voltage application in the comparative example.
Figure 14C:
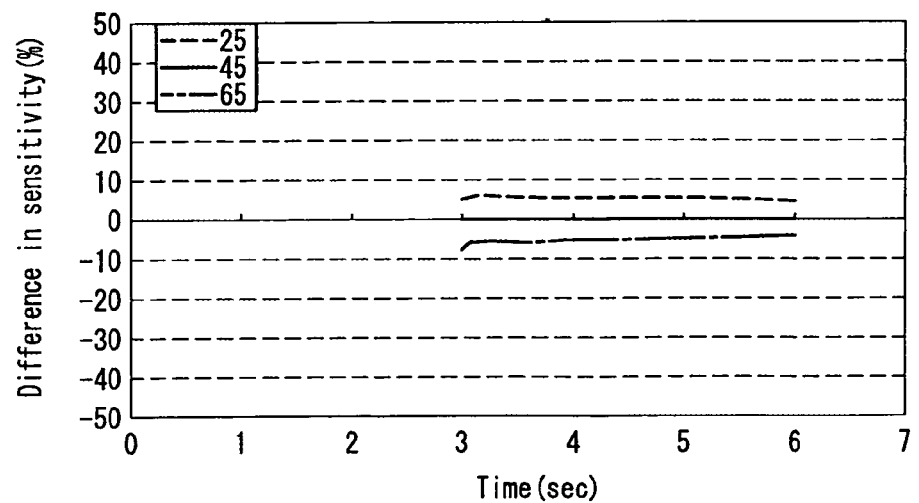
FIG. 14C is a graph showing changes in difference in sensitivity (%) over time during the voltage application in the comparative example.
Figure 16A:
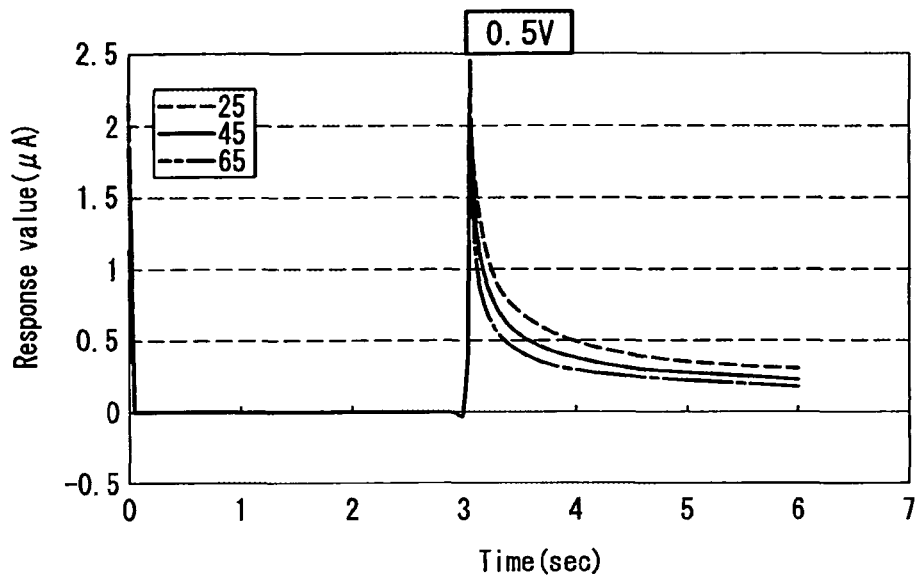
FIG. 16A is a graph showing changes in response current (μA) obtained in Hct measurement over time during voltage application (0.5 V) in still another example of a sensor according to the present invention.
Figure 16B:
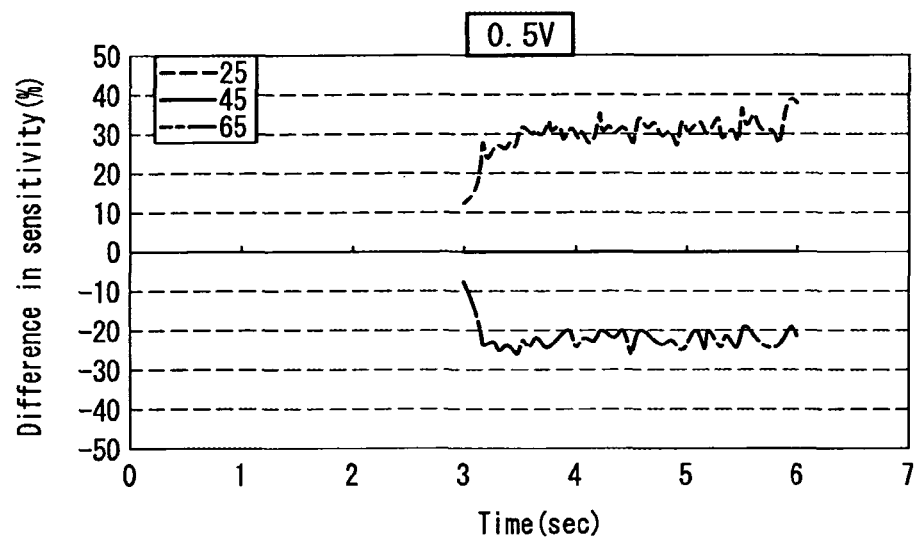
FIG. 16B is a graph showing changes in difference in sensitivity (%) over time during the voltage application in the example.
Figure 17A:
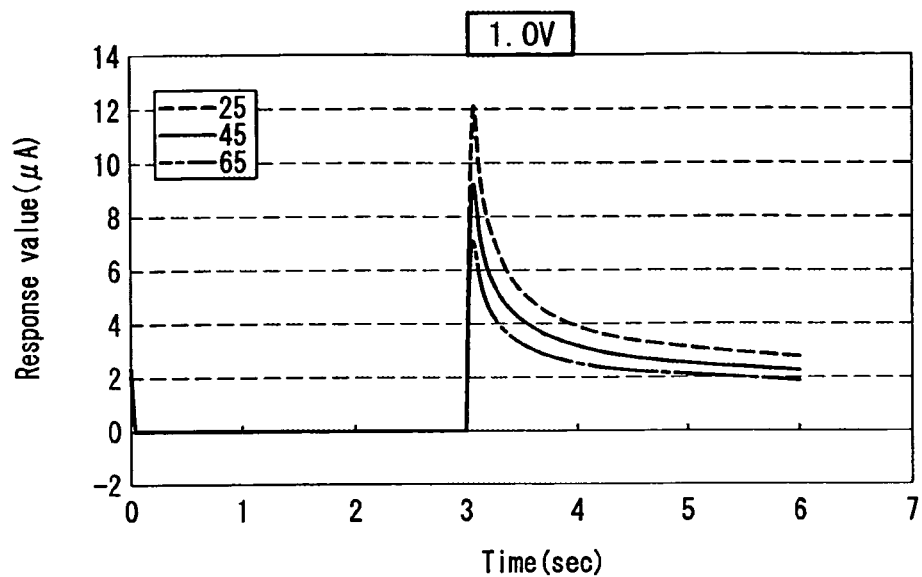
FIG. 17A is a graph showing changes in response current (μA) obtained in Hct measurement over time during voltage application (1.0 V) in still another example of a sensor according to the present invention.
Figure 17B:
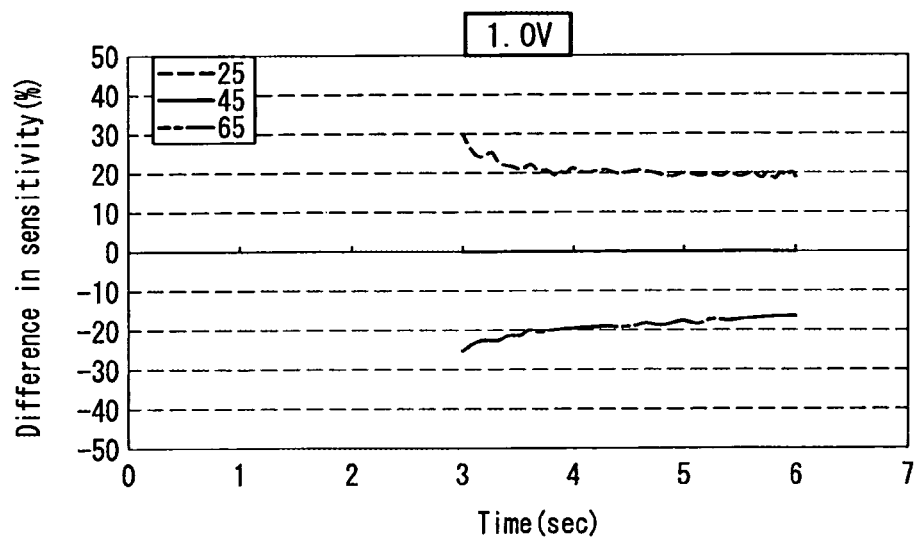
FIG. 17B is a graph showing changes in difference in sensitivity (%) over time during the voltage application in the example.
Figure 18A:
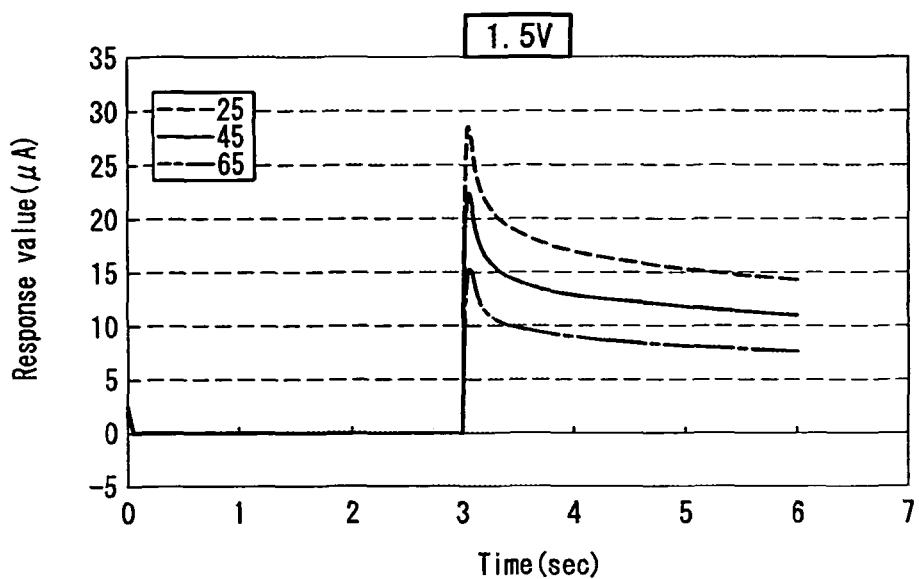
FIG. 18A is a graph showing changes in response current (μA) obtained in Hct measurement over time during voltage application (1.5 V) in still another example of a sensor according to the present invention.
Figure 18B:
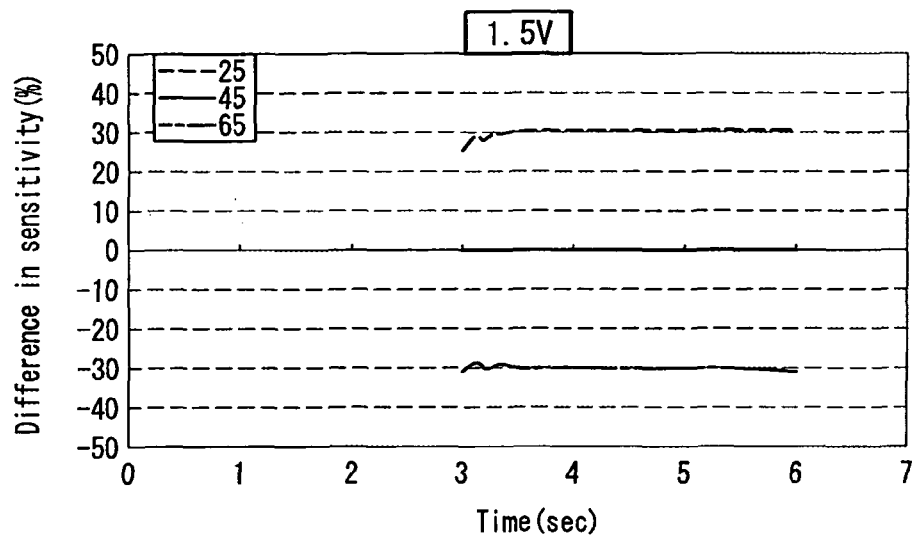
FIG. 18B is a graph showing changes in difference in sensitivity (%) over time during the voltage application in the example.
Figure 19A:
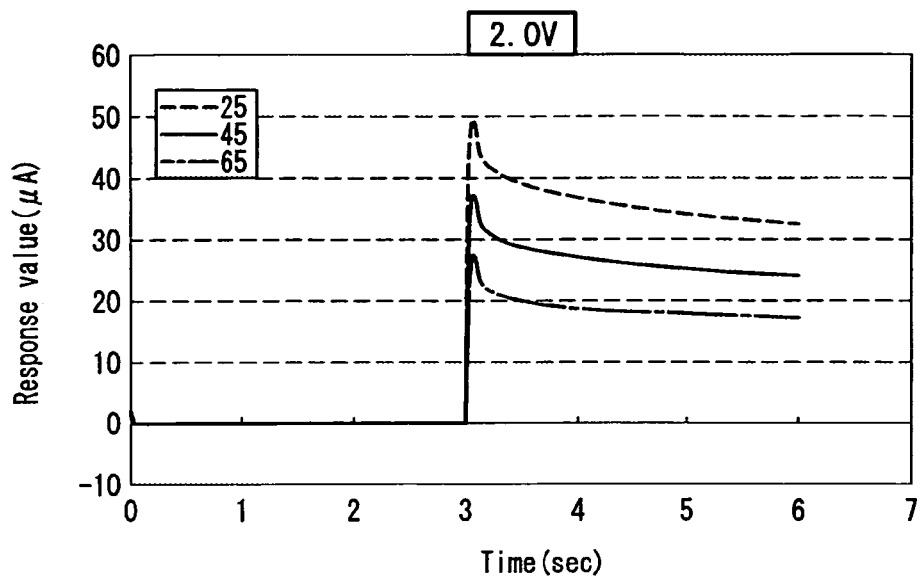
FIG. 19A is a graph showing changes in response current (μA) obtained in Hct measurement over time during voltage application (2.0 V) in still another example of a sensor according to the present invention.
Figure 19B:
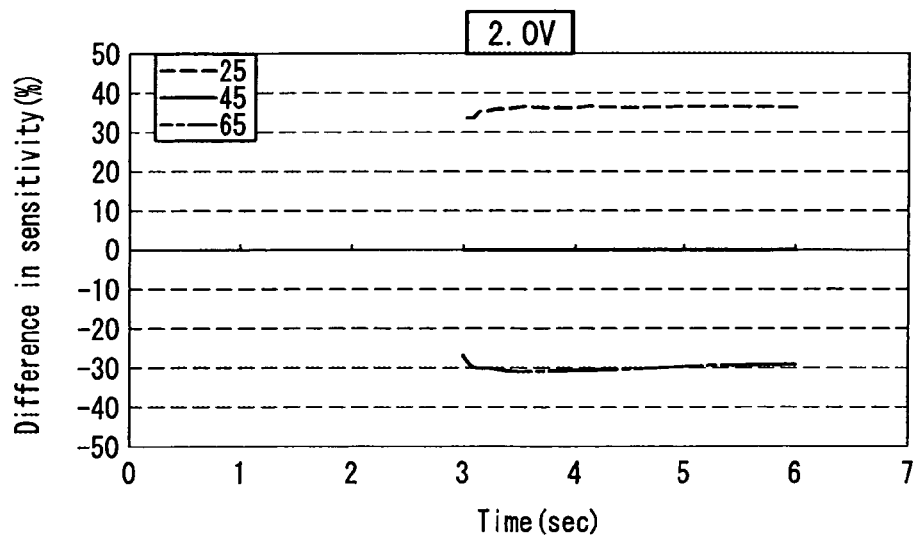
FIG. 19B is a graph showing changes in difference in sensitivity (%) over time during the voltage application in the example.
Figure 20A:
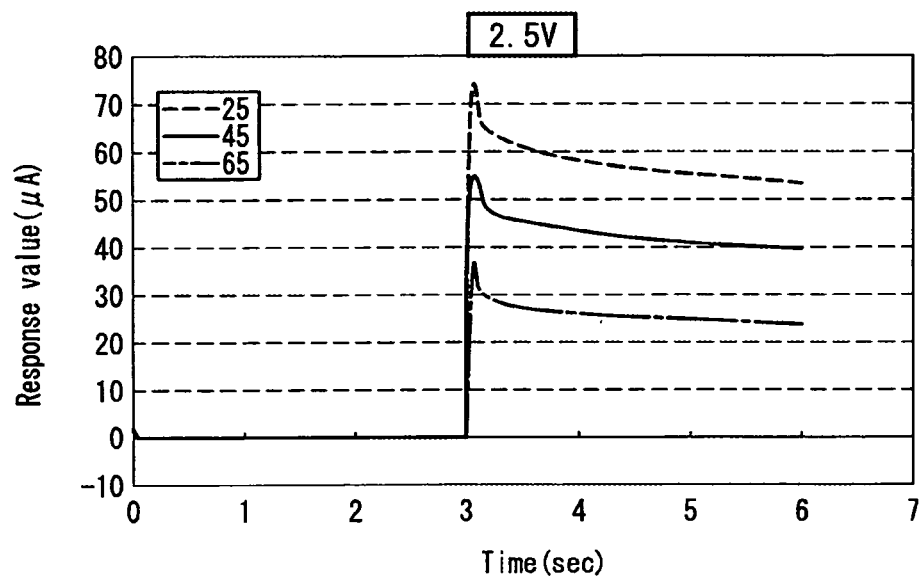
FIG. 20A is a graph showing changes in response current (μA) obtained in Hct measurement over time during voltage application (2.5 V) in still another example of a sensor according to the present invention.
Figure 20B:
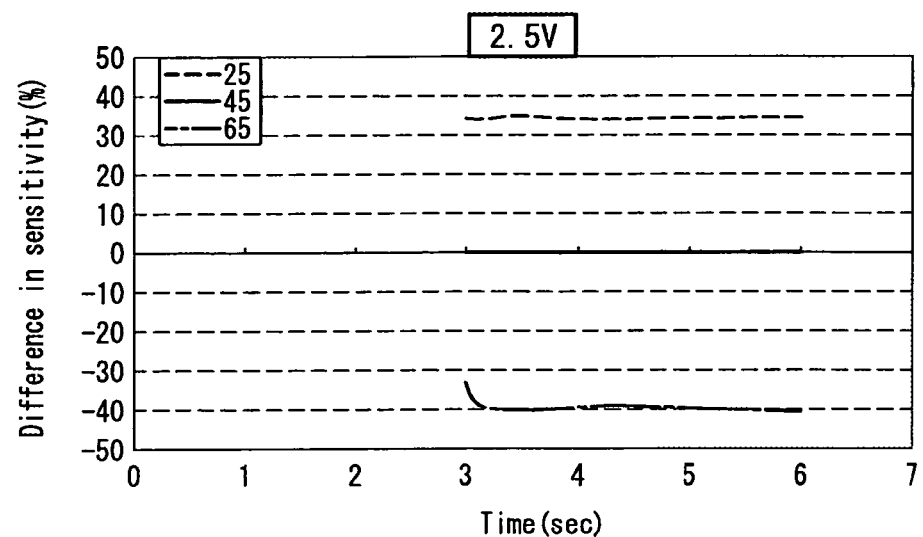
FIG. 20B is a graph showing changes in difference in sensitivity (%) over time during the voltage application in the example.
Figure 21A:
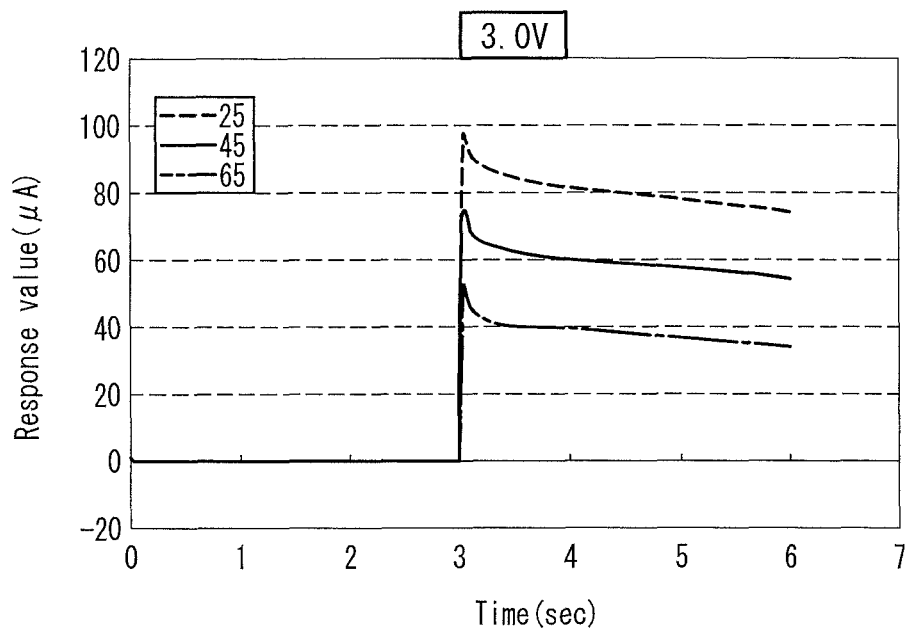
FIG. 21A is a graph showing changes in response current (μA) obtained in Hct measurement over time during voltage application (3.0 V) in still another example of a sensor according to the present invention.
Figure 21B:
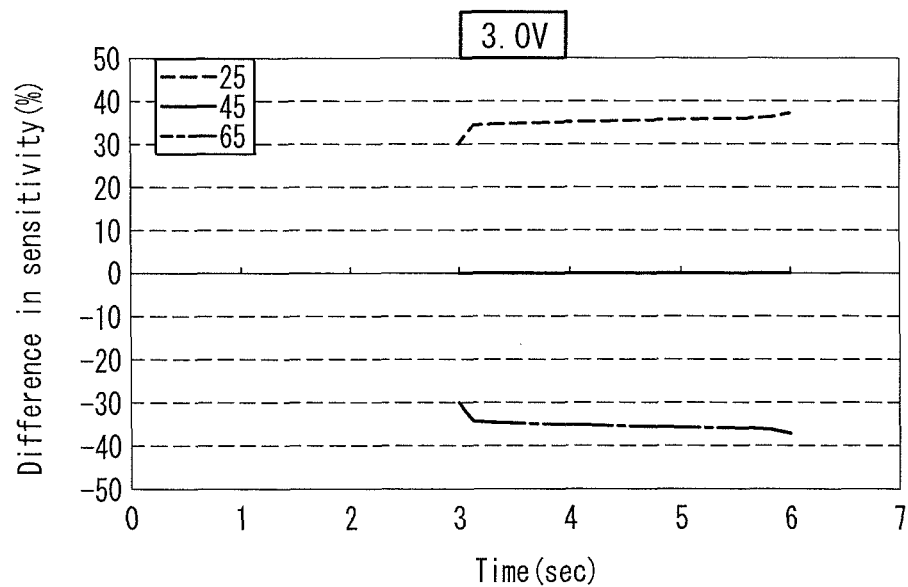
FIG. 21B is a graph showing changes in difference in sensitivity (%) over time during the voltage application in the example.
Figure 22A:
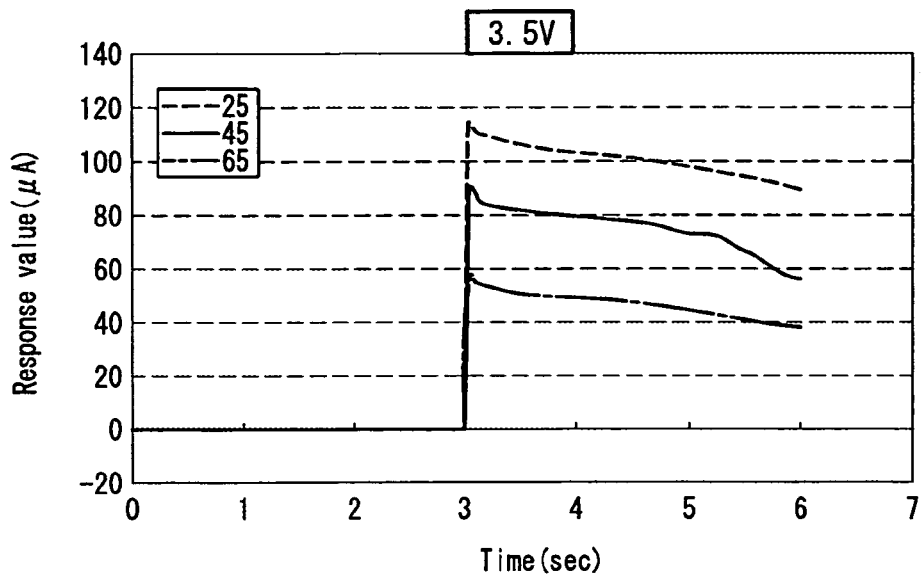
FIG. 22A is a graph showing changes in response current (μA) obtained in Hct measurement over time during voltage application (3.5 V) in still another example of a sensor according to the present invention.
Figure 22B:
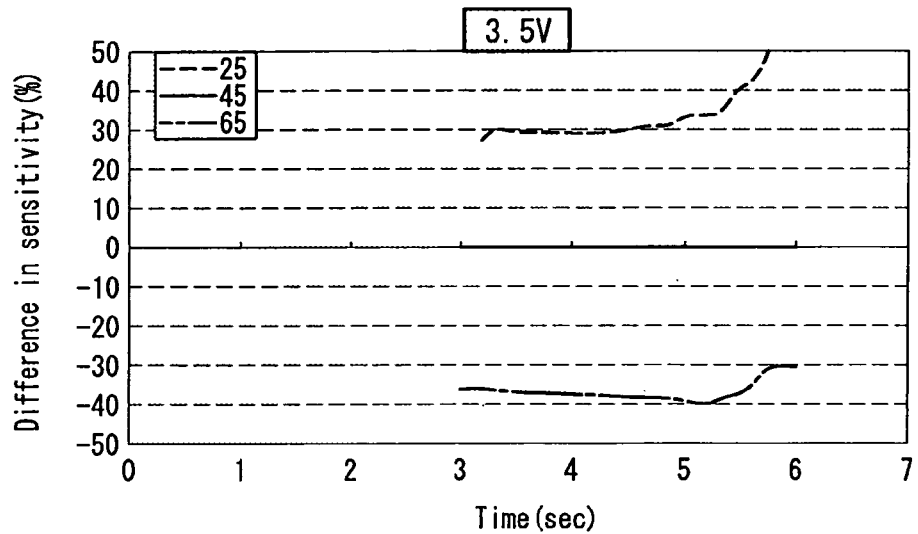
FIG. 22B is a graph showing changes in difference in sensitivity (%) over time during the voltage application in the example.
Figure 23A:
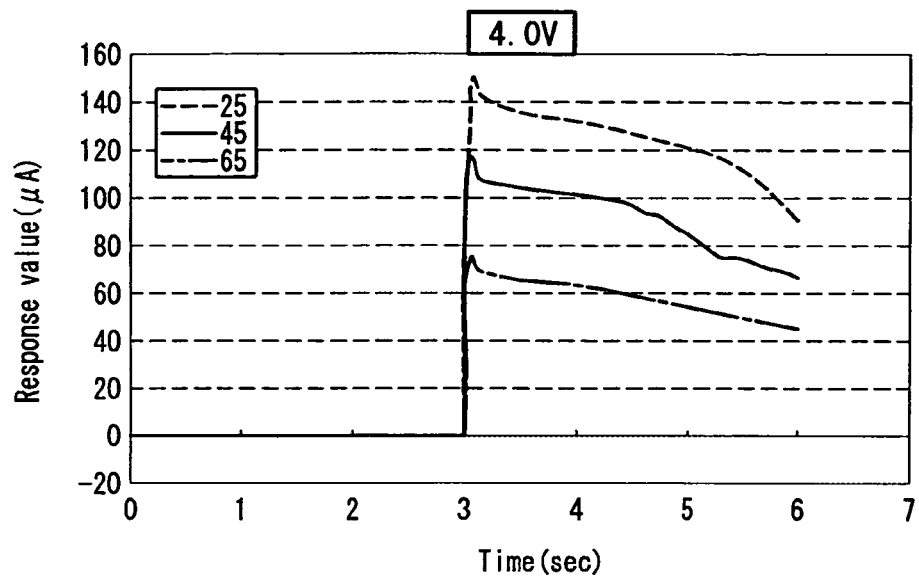
FIG. 23A is a graph showing changes in response current (μA) obtained in Hct measurement over time during voltage application (4.0 V) in still another example of a sensor according to the present invention.
Figure 23B:
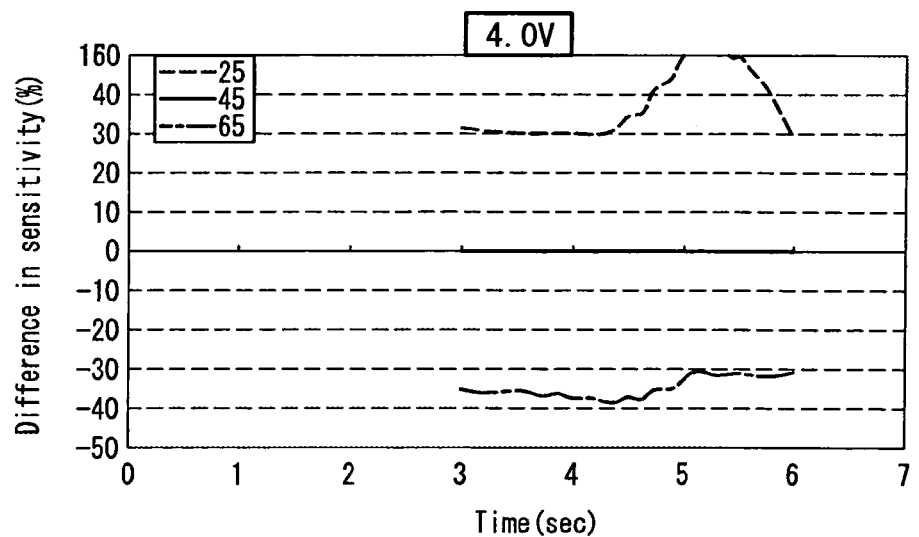
FIG. 23B is a graph showing changes in difference in sensitivity (%) over time during the voltage application in the example.
Figure 24A:
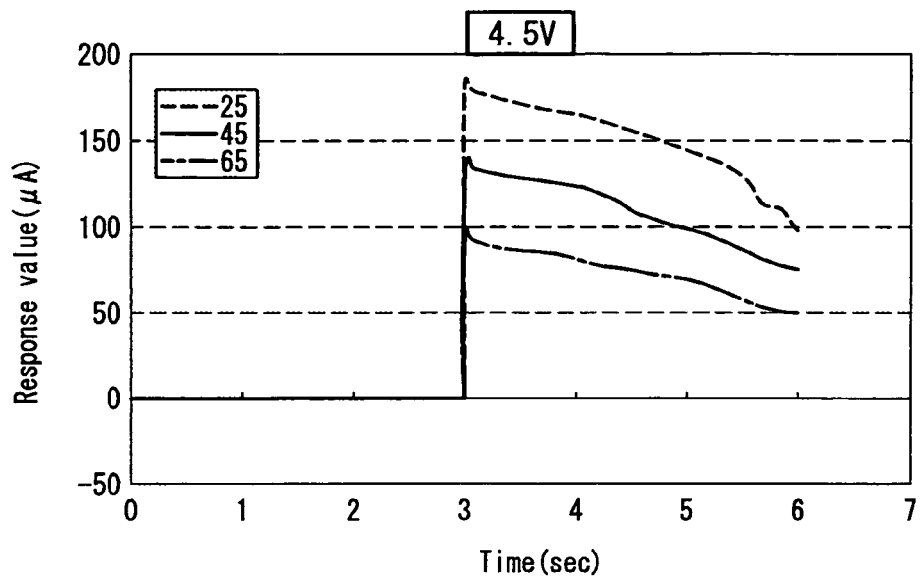
FIG. 24A is a graph showing changes in response current (μA) obtained in Hct measurement over time during voltage application (4.5 V) in still another example of a sensor according to the present invention.
Figure 24B:
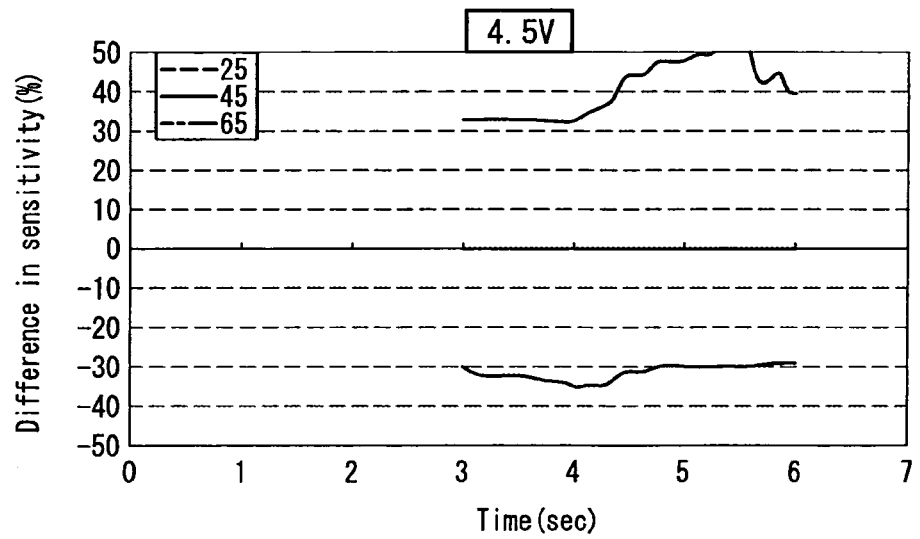
FIG. 24B is a graph showing changes in difference in sensitivity (%) over time during the voltage application in the example.
Figure 25A:
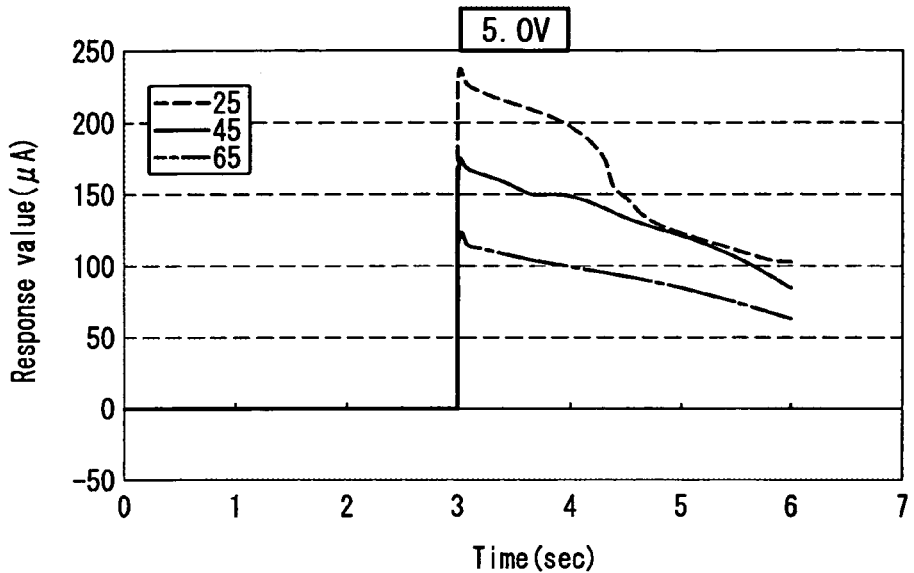
FIG. 25A is a graph showing changes in response current (μA) obtained in Hct measurement over time during voltage application (5.0 V) in still another example of a sensor according to the present invention.
Figure 25B:
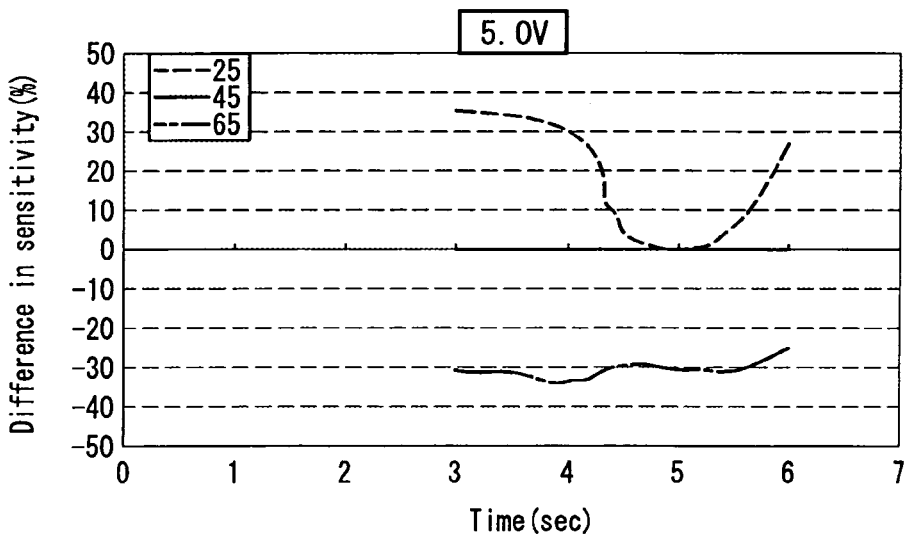
FIG. 25B is a graph showing changes in difference in sensitivity (%) over time during the voltage application in the example.
Figure 26A:
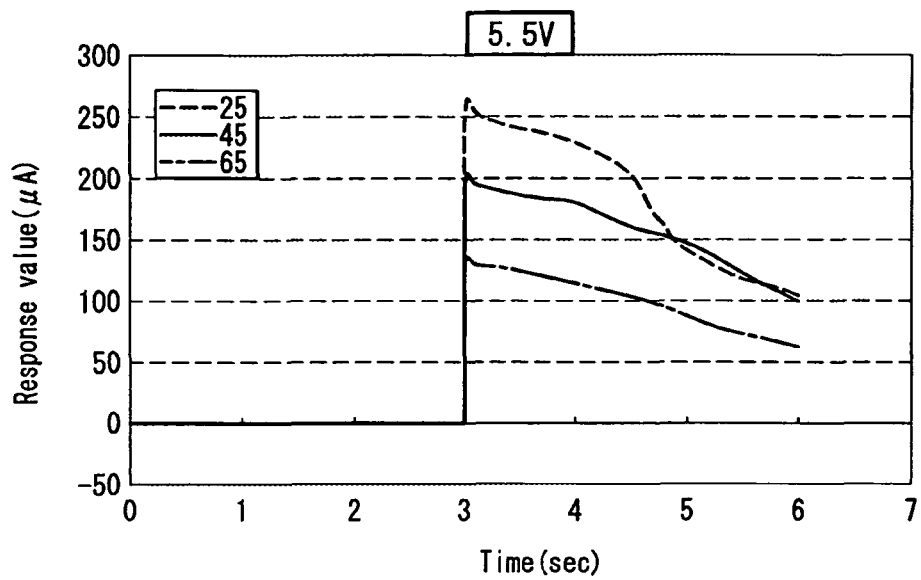
FIG. 26A is a graph showing changes in response current (μA) obtained in Hct measurement over time during voltage application (5.5 V) in still another example of a sensor according to the present invention.
Figure 26B:
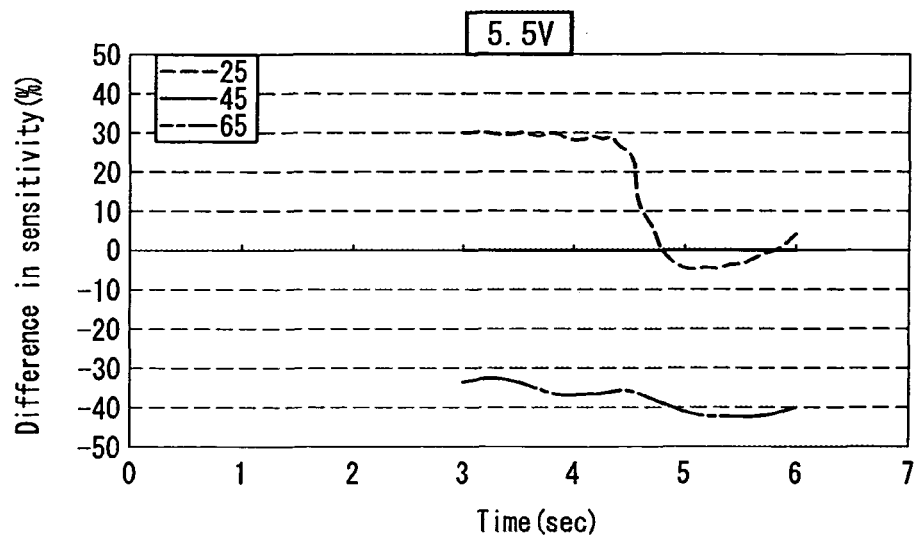
FIG. 26B is a graph showing changes in difference in sensitivity (%) over time during the voltage application in the example.
Figure 27A:
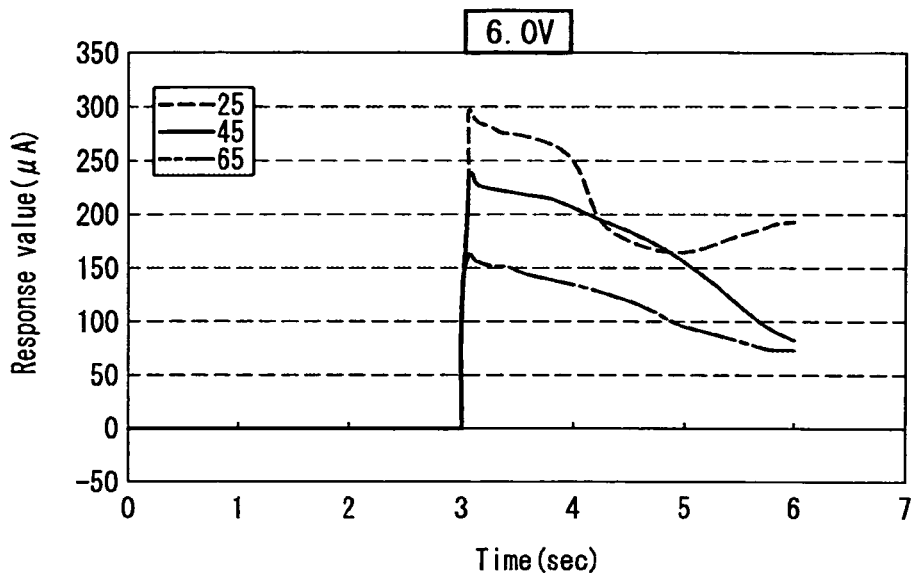
FIG. 27A is a graph showing changes in response current (μA) obtained in Hct measurement over time during voltage application (6.0 V) in still another example of a sensor according to the present invention.
Figure 27B:
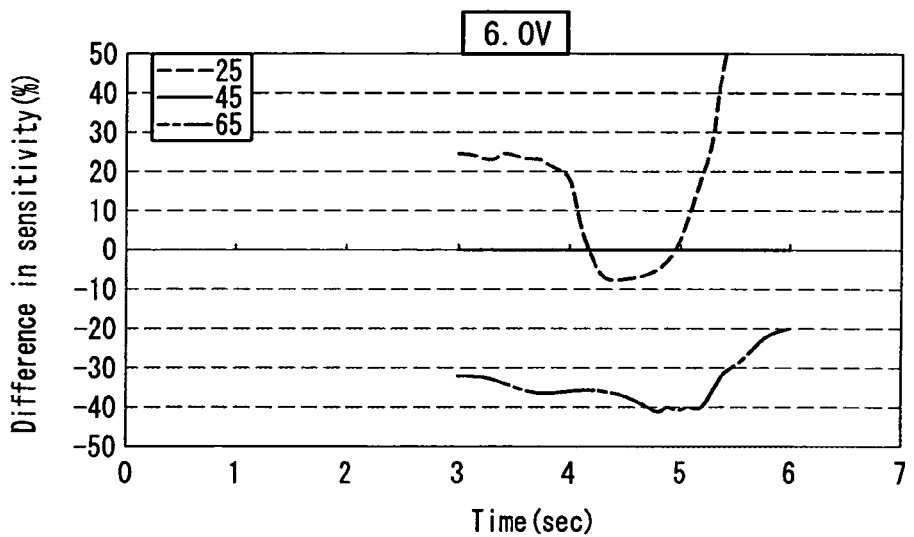
FIG. 27B is a graph showing changes in difference in sensitivity (%) over time during the voltage application in the example.
Figure 28A:
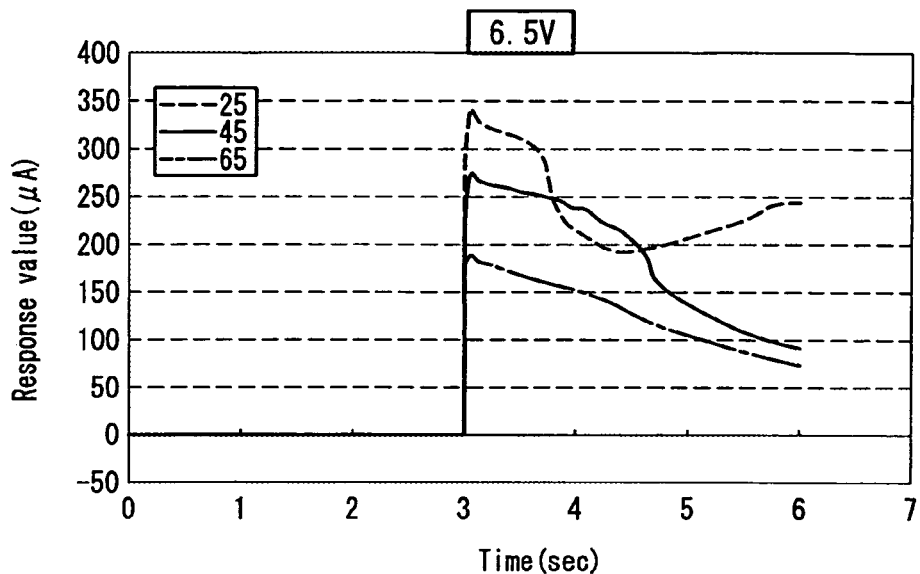
FIG. 28A is a graph showing changes in response current (μA) obtained in Hct measurement over time during voltage application (6.5 V) in still another example of a sensor according to the present invention.
Figure 28B:
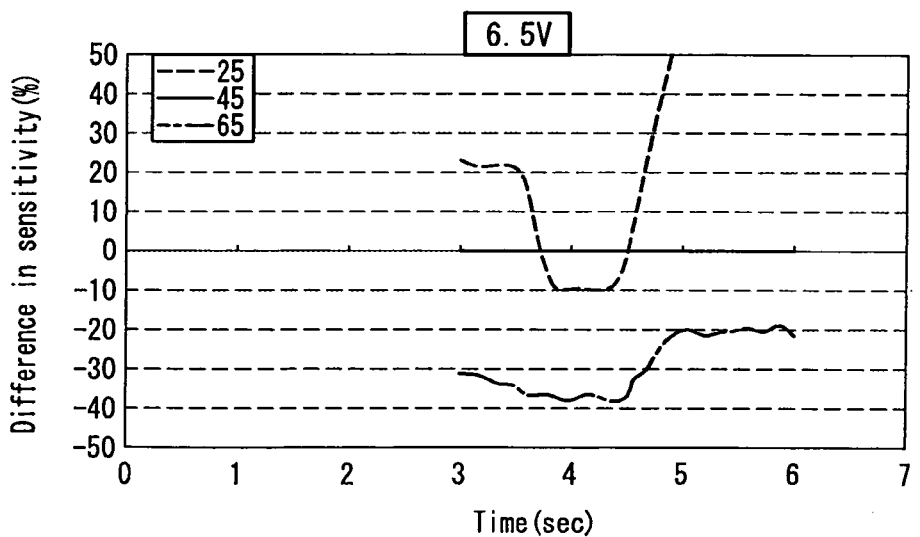
FIG. 28B is a graph showing changes in difference in sensitivity (%) over time during the voltage application in the example.

As shown in FIG. 14A, in the sensor of this comparative example, the reagent layers 25 were provided so as to lie over the working electrode 24 and the counter electrode 21, respectively, and these reagent layers 25 were also present at a part of the region between these electrodes. The graphs of FIGS. 14B and 14C show the results of the measurement of the current flowing between the electrodes of this sensor. As shown in FIGS. 14B and 14C, according to this sensor, the response current reflecting the Hct value could not be detected definitely.

(3-9)

As shown in FIG. 15A, in the sensor of this comparative example, the reagent layer 25 was not provided. The graphs of FIGS. 15B and 15C show the results of the measurement of the current flowing between the electrodes of this sensor. As shown in FIGS. 15B and 15C, according to this sensor, the response current reflecting the Hct value could not be detected.

Example 4

In the present example, the response current and the difference in sensitivity in the Hct measurement were measured at various applied voltages in the range from 0.5 to 6.5 V. The preparation of the specimens (blood), the measurement of glucose, and the correction of the blood component were carried out in the same manner as in Example 2. The sensor used for this measurement was produced in the same manner as in Example 3. Note here that the reagent layer 25 was provided on the counter electrode 21 but not on the working electrode 24 (see FIG. 7A). Furthermore, the response current and the difference in sensitivity were measured in the same manner as in Example 3. The results of the measurement are shown in the graphs of FIGS. 16 to 28. In FIGS. 16 to 28, FIGS. 16A to 28A are graphs each showing changes in response current (μA) over time during the application of the voltage (V), and FIGS. 16B to 28B are graphs each showing changes in difference in sensitivity (%) over time during the application of the voltage (V).

As shown in FIG. 16, even when the applied voltage was 0.5 V, it was possible to detect the response current reflecting the Hct value. However, as shown in FIGS. 17 to 28, the response current could be measured still more definitely when the applied voltage was in the range from 1 to 6.5 V. Furthermore, as shown in FIGS. 17 to 21, the most preferable results were obtained when the applied voltage was in the range from 1 to 3 V. When the applied voltage was 5 V or more, the distortion of the waveform occurred with the passage of time However, within a short time immediately after the start of the voltage application, the response current reflecting the Hct value could be detected definitely. Although the present example is directed to the case where the current based on a Hct value was measured with various applied voltages under fixed conditions, the present invention is not limited thereto. It should be noted that even when the applied voltage is outside the range shown in the present example, it is still possible to detect the response current reflecting the Hct value definitely by setting other conditions such as the distance between the electrodes and the amount and the type of the redox substance as appropriate, and the amount of the blood component can be corrected based on the thus-detected Hct value.

Example 5

Figure 30:
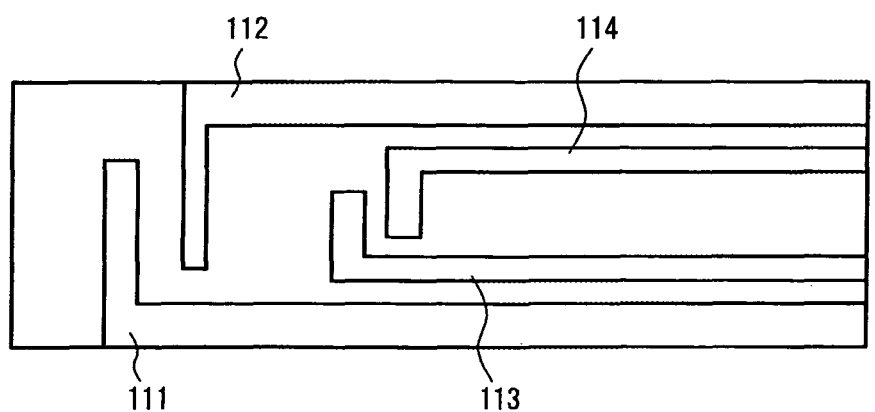
FIG. 30 is a plan view showing still another example of a sensor according to the present invention.

FIG. 30 is a plan view showing still another example of a sensor of the present invention. This sensor has an electrode pattern different from those of the sensors according to Examples 1 to 4. As shown in FIG. 30, this sensor includes, on an insulating substrate, two electrodes 111 and 112 composing a second analysis portion used for Hct measurement on an upstream side and two electrodes 113 and 114 composing a first analysis portion used for blood component measurement on a downstream side with respect to the flow of blood. In this sensor, reagent layers (not shown) are provided on the first analysis portion and the second analysis portion, respectively. The reagent layer provided on the first analysis portion contains an oxidoreductase such as glucose dehydrogenase and a mediator and optionally contains a polymeric material, an enzyme stabilizer, and a crystal homogenizing agent, and the arrangement thereof is not particularly limited. On the other hand, the reagent layer provided on the second analysis portion contains a mediator and optionally contains a polymeric material. In the second analysis portion, the reagent layer is provided only on the counter electrode. Other than the above, the configuration of the sensor according to the present example is the same as that of the sensor according to Example 1 or 2.

Figure 31:
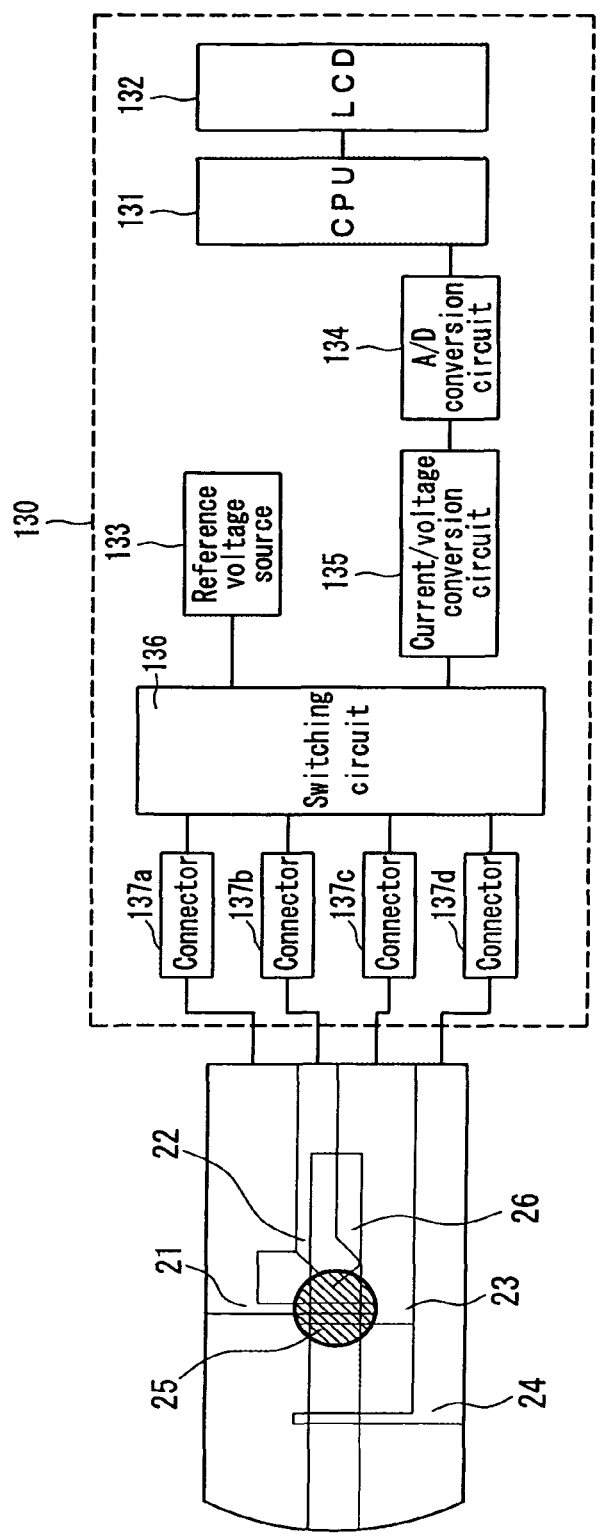
FIG. 31 is a plan view showing the configuration of the measuring device according to the above example.

Next, FIG. 31 shows an example of the configuration of a measuring device according to the present invention. For example, the sensor shown in Example 2 can be attached to this measuring device. As shown in FIG. 31, this measuring device 130 includes four connectors 137a to 137d, a switching circuit 136, a current/voltage conversion circuit 135, an A/D conversion circuit 134, a reference voltage source 133, a CPU 131, and a liquid crystal display (LCD) 132 as main components. Note here that the reference voltage source 133 may be grounded. The electrodes 21, 22, 23, and 24 of the sensor are connected to the current/voltage conversion circuit 135 and the reference voltage source 133 via the connectors 137a to 137d and the switching circuit 136. The current/voltage conversion circuit 135 is connected to the CPU 131 via the A/D conversion circuit 134.

In this measuring device, measurement of the amount of a blood component can be carried out in the following manner, for example.

First, in accordance with an instruction from the CPU 131, the switching circuit 136 connects the electrode 21 serving as a working electrode for blood component measurement to the current/voltage conversion circuit 135 via the connector 137a and connects the electrode 22 serving as a detecting electrode for detecting the supply of blood to the reference voltage source 133 via the connector 137b. When a constant voltage is applied between the electrode 21 and the electrode 22 from the current/voltage conversion circuit 135 and the reference voltage source 133 in accordance with an instruction from the CPU 131 and blood is supplied to the sensor in this state, a current flows between the electrodes 21 and 22. This current is converted into a voltage by the current/voltage conversion circuit 135, and the value of this voltage is converted into a digital value by the A/D conversion circuit 134 and is output to the CPU 131. Based on this digital value, the CPU 131 detects the supply of the blood.

After the supply of the blood has been detected, the amount of the blood component is measured. The measurement of the amount of the blood component is carried out in the following manner, for example. First, in accordance with an instruction from the CPU 131, the switching circuit 136 connects the electrode 21 serving as a working electrode for blood component measurement to the current/voltage conversion circuit 135 via the connector 137a and connects the electrode 23 serving as a counter electrode for blood component measurement to the reference voltage source 133 via the connector 137c.

The current/voltage conversion circuit 135 and the reference voltage source 133 are turned off, for example, while glucose in the blood is allowed to react with the oxidoreductase for a certain period of time, and after a lapse of a certain period of time, a constant voltage is applied between the electrodes 21 and 23 in accordance with an instruction from the CPU 131. A current flows between the electrodes 21 and 23, and this current is converted into a voltage by the current/voltage conversion circuit 135. The value of this voltage is converted into a digital value by the A/D conversion circuit 134 and is output to the CPU 131. The CPU 131 converts this digital value to the amount of the blood component.

After the amount of the blood component has been measured, a Hct value is measured. The measurement of a Hct value is carried out in the following manner, for example. First, in accordance with an instruction from the CPU 131, the switching circuit 136 connects the electrode 24 serving as a working electrode for Hct measurement to the current/voltage conversion circuit 135 via the connector 137d and connects the electrode 21 serving as a counter electrode for Hct measurement to the reference voltage source 133.

Then, in accordance with an instruction from CPU 131, a constant voltage is applied between the electrodes 24 and 21 from the current/voltage conversion circuit 135 and the reference voltage source 133. The current flowing between the electrodes 24 and 21 is converted into a voltage by the current/voltage conversion circuit 135, and the value of this voltage is converted into a digital value by the A/D conversion circuit 134 and is output to the CPU 131. The CPU 131 converts the digital value into a Hct value.

Using the Hct value and the amount of the blood component obtained in the above measurements, the amount of the blood component is corrected using the Hct value with reference to a calibration curve or a calibration curve table prepared previously, and the corrected amount of the blood component is displayed in the LCD 132.

Although the present invention has been described with reference to the examples where glucose is measured, the present invention is not limited thereto. As already described above, the present invention also is useful for the measurement of other blood components, such as lactic acid and cholesterol. Moreover, according to the measurement method and the sensor of the present invention, a current response corresponding to the type of a sample supplied to the sensor is obtained. This allows the type of a sample to be identified based on the result obtained. Therefore, according to the measurement method and the sensor of the present invention, it is possible to identify, for example, a standard solution for calibrating the sensor, blood plasma, and blood easily.

INDUSTRIAL APPLICABILITY

As specifically described above, according to a method of measuring a blood component, a sensor used in the method, and a measuring device of the present invention, a Hct value can be measured electrochemically and easily with high accuracy and high reliability and the amount of the blood component can be corrected based on the Hct value. Therefore, the measurement method, the sensor, and the measuring device of the present invention can be used suitably to all the technical fields in which the measurement of a blood component is required, such as biology, biochemistry, and medical science, and are particularly suitable in the field of clinical tests.

The invention claimed is:

1. A method of measuring a component in a blood sample, comprising:
    causing a redox reaction between the component in the blood sample and an oxidoreductase in the presence of a mediator;
    detecting a first oxidation current or a reduction current caused by the redox reaction with an electrode system for measuring the component;
    calculating an amount of the component based on a value of the detected current; and
    measuring a Hct value of the blood sample and correcting the amount of the component using the measured Hct value, the measurement of the Hct value comprising:
        applying a voltage in the presence of the blood sample to a second electrode system for Hct value measurement that comprises a counter electrode and a working electrode to cause an oxidation current or a reduction current to flow between the counter electrode and the working electrode for the Hct value measurement, the oxidoreductase and the mediator used for the redox reaction with the component in the blood sample being present on the counter electrode for the Hct value measurement, the counter electrode for the Hct value measurement being part of the first electrode system for detecting the oxidation or reduction current for measuring the component in the blood sample, and a mediator for the Hct value measurement being present on the counter electrode for Hct value measurement and not on the working electrode for Hct value measurement;
        detecting the oxidation current or the reduction current from applying the voltage to the electrode system for Hct measurement; and
        calculating the Hct value based on a value of the detected current.

2. The method according to claim 1, wherein the mediator used for the measurement of the Hct value is a ferricyanide.

3. The method according to claim 2, wherein the ferricyanide is potassium ferricyanide.

4. The method according to claim 1, wherein the working electrode for measuring the Hct value is coated with a polymeric material.

5. The method according to claim 4, wherein the polymeric material is carboxymethylcellulose.

6. The method according to claim 1, wherein the voltage applied in the measurement of the Hct value is equal to or higher than a voltage causing electrolysis of water.

7. The method according to claim 6, wherein the voltage applied in the measurement of the Hct value is 1 to 10 V.

8. The method according to claim 7, wherein the voltage applied in the measurement of the Hct value is 1 to 6.5 V.

9. The method according to claim 1, wherein the correction using the Hct value is carried out based on one of a calibration curve and a calibration table prepared previously for showing a relationship between a Hct value and an amount of the component.

10. The method according to claim 1, wherein the Hct value is measured after the amount of the component has been measured.

11. The method according to claim 1, further comprising measuring a temperature of a measurement environment, wherein the amount of the component is corrected using the measured temperature.

12. The method according to claim 1, further comprising measuring a temperature of a measurement environment, wherein the amount of the component is corrected using the measured temperature and the correction using the temperature is carried out based on one of a calibration curve and a calibration table that have been prepared previously for showing a relationship between a blood temperature and an amount of the component.

13. The method according to claim 1, wherein the component to be measured is at least one selected from the group consisting of glucose, lactic acid, uric acid, bilirubin, and cholesterol.

14. The method according to claim 13, wherein the component to be measured is glucose, and the oxidoreductase is at least one of glucose oxidase and glucose dehydrogenase.

15. The method according to claim 1, wherein the application of voltage for the Hct measurement is carried out for a time period of 0.01 to 10 seconds.

16. The method according to claim 1, wherein the working electrode for the Hct value measurement is not affected by the mediator on the counter electrode during the Hct value measurement.

* * * * *